US010011689B2

(12) United States Patent
Park et al.

(10) Patent No.: US 10,011,689 B2
(45) Date of Patent: Jul. 3, 2018

(54) HYDROGEL TISSUE EXPANDERS

(71) Applicants: Akina, Inc., West Lafayette, IN (US);
The United States of America, as Represented by the Department of Veterans Affairs, Washington, DC (US)

(72) Inventors: Kinam Park, West Lafayette, IN (US);
Clark Tobias Barco, Martinsville, IN (US); Haesun Park, West Lafayette, IN (US); Yourong Fu, Ashburn, VA (US);
John Solomon Garner, West Lafayette, IN (US)

(73) Assignees: Akina, Inc., West Lafayette, IN (US);
THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 15/304,495

(22) PCT Filed: Apr. 13, 2015

(86) PCT No.: PCT/US2015/025556
§ 371 (c)(1),
(2) Date: Oct. 14, 2016

(87) PCT Pub. No.: WO2015/160699
PCT Pub. Date: Oct. 22, 2015

(65) Prior Publication Data
US 2017/0037196 A1 Feb. 9, 2017

Related U.S. Application Data

(60) Provisional application No. 61/979,080, filed on Apr. 14, 2014.

(51) Int. Cl.
| | | |
|---|---|---|
| *C08J 3/075* | (2006.01) | |
| *C08G 81/00* | (2006.01) | |
| *A61C 8/02* | (2006.01) | |
| *A61B 90/00* | (2016.01) | |
| *A61F 2/28* | (2006.01) | |
| *A61K 47/34* | (2017.01) | |
| *C08F 299/02* | (2006.01) | |
| *A61B 17/88* | (2006.01) | |
| *A61B 17/68* | (2006.01) | |
| *A61B 17/00* | (2006.01) | |

(52) U.S. Cl.
CPC .............. *C08J 3/075* (2013.01); *A61B 90/02* (2016.02); *A61C 8/0006* (2013.01); *A61F 2/2803* (2013.01); *A61K 47/34* (2013.01); *C08F 299/024* (2013.01); *C08G 81/00* (2013.01); *A61B 17/8858* (2013.01); *A61B 2017/00004* (2013.01); *A61B 2017/00898* (2013.01); *A61B 2017/681* (2013.01); *A61F 2310/00383* (2013.01); *C08J 2353/00* (2013.01)

(58) Field of Classification Search
None
See application file for complete search history.

(56) References Cited

U.S. PATENT DOCUMENTS

| | | | |
|---|---|---|---|
| 5,496,368 A | 3/1996 | Wiese | |
| 7,297,348 B2 * | 11/2007 | Li | ......................... A61K 9/0024 424/485 |
| 8,211,959 B2 * | 7/2012 | Shen | ...................... C08G 63/08 523/423 |
| 2004/0077797 A1 | 4/2004 | Asgarzadeh et al. | |
| 2007/0031499 A1 * | 2/2007 | Huh | ..................... C08B 37/003 424/486 |

FOREIGN PATENT DOCUMENTS

WO    WO 2011/110407 A2    9/2011

OTHER PUBLICATIONS

PCT ISA/US International search report for PCT/US2015/025556, dated Aug. 7, 2015.
S.R. Baker, "Fundamentals of expanded tissue," Head Neck, (1991) 13(4): 327-33.
H. Jhuma, et al., "Repair of a cheek defect with the tissue expander method: A case report," Bull. Tokyo Dent. Coll., (1997) 38(4): pp. 311-316.
O. Antonyshyn, et al., Tissue expansion in head and neck reconstruction. Plast. Reconstr. Surg., (1988) 82(1): pp. 58-68.
J.B. Wieslander, "Tissue expansion in the head and neck: A 6-year review," Scand. J. Plast. Reconstr. Surg., (1991) 25(1): pp. 47-56.
J.T. Chun and R. J.Rohrich, "Versatility of tissue expansion in head and neck burn reconstruction," Ann. Plast. Surg., (1998)41(1): pp. 11-16.
S.E. MacLennan, et al., "Tissue expansion in head and neck burn reconstruction," Clin. Plast. Surg., (2000) 27(1): pp. 121-132.
R. Newman and D. C. Cleveland, "Three-dimensional reconstruction of ultrafast chest CT for diagnosis and operative planning in a child with right pneumonectomy syndrome," (1994) 106(3): pp. 973-974.
V. I. Sharobaro, et al., "First experience of endoscopic implantation of tissue expanders in plastic and reconstructive surgery," Surg. Endosc., (2004) 17(12) pp. 513-517.
B. S. Bauer, "The role of tissue expansion in reconstruction of the ear," Clin. Plast. Surg., (1990) 17(2): pp. 319-325.

(Continued)

Primary Examiner — Robert A Wax
Assistant Examiner — Quanglong N Truong
(74) Attorney, Agent, or Firm — E. Victor Indiano; Indiano & McConnell, LLC

(57) ABSTRACT

The present invention provides tissue expanders comprising biodegradable, chemically cross-linked hydrogels which are elastic in the dry state. These biocompatible tissue expanders are self-inflating and membrane-free. They swell slowly and elicit minimal negative tissue responses, while allowing for rapid and easy manipulation by the surgeon at the time of emplacement.

17 Claims, 7 Drawing Sheets

(56) References Cited

OTHER PUBLICATIONS

R. L. Simpson and M. E. Flaherty, "The burned small finger," Clin. Plast. Surg., (1992) 19)3): pp. 673-682.

R. Silfen, et al., "Tissue expansion for frontal hairline restoration in severe alopecia in a child," Burns, (2000) 26(3): pp. 294-297.

T.O. Acarturk, et al., "Reconstruction of difficult wounds with tissue-expanded free flaps," Ann. Plast. Surg., (2004) 52 (5): pp. 493-499.

P. Rosselli, et al., "Use of a soft tissue expander before surgical treatment of clubfoot in children and adoleseecnts," J. Pediatr. Orthop., (2005) 25(3): pp. 353-356.

K. F. Kobus, "Cleft palate repair with the use of osmotic expanders: A preliminary report," Journal of Plastic, Reconstructive & Aesthetic Surgery, (2007) 60: pp. 414-421.

S. J. Berge, et al., "Tissue expansion using osmotically active hydrogel systems for direct closure of the donor defect of the radial forearm flap," Plast. Reconstr. Surg., (2001) 108(1): pp. 1-5, discussion pp. 6-7).

D. Lew, et al., "Use of a soft tissue expander in alveolar ridge augmentation: A preliminary report," J. Oral Maxillofac. Surg., (1986) 44(7): pp. 516-519.

T. M. Hassan, "Mandibular alveolar ridge augmentatioin using a soft tissue expander: Report of case," J. Conn. State Dent. Assoc., (1988) 62(3): pp. 130-134.

D. Lew, et al., "An open procedure for placement of a tissue expander over the atrophic alveolar ridge," J. Oral Maxillofac. Surg., (1988) 46 (2): pp. 161-166.

A. R. Wittkampf, "Short-term experience with the subperiosteal tissue expander in reconstruction of the mandibular alveolar ridge," J. Oral Maxillofac. Surg., (1989) 47(5): pp. 469-474.

A.A. Quayle, et al., "Alveolar ridge augmentation using a new design of inflatable tissue expander: Surgical technique and preliminary results," Br. J. Oral Maxillofac. Surg., (1990) 28(6): pp. 375-382.

H. C. Schwartz and R. J. Relle, "Extraoral placement of a subperiosteal tissue expander for reconstruction with hydroxylapatite of the severely atrophic mandibular alveolar ridge," J. Oral Maxillofac. Surg., (1990) 48(2): pp. 157-161.

D. Lew, et al., "Use of subperiosteal implants with distal filling ports in the correction of the atrophic alveolar ridge," Int. J. Oral Maxillofac. Surg., (1991) 20(1); pp. 15-17.

D. J. Zeiter, et al., "The use of a soft tissue expander in an alveolar bone ridge augmentation for implant placement," Int. J. Periodontics Restorative Dent., (1998) 18(4): pp. 403-409.

J.M. Vlassis, et al., "Controlled subperiosteal tissue expansion to facilitate GBR for the placement of endosseous dental implants," Int. J. Periodontics Restorative Dent., (1999) 19(3): pp. 289-297.

K. Tominaga, et al., "An animal model for subperiosteal tissue expansion," J. Oral Maxillofac. Surg., (1993) 51(11): pp. 1244-1249.

M. B. Hurzeler, et al., "Guided bone regeneration around dental implants in the atrophic alveolar ridge using a bioresorbable barrier: An experimental study in the monkey," Clin. Oral Implants Res., (1997) 8(4): pp. 323-331.

B. A. Feldt, et al., "The joint facial and invasive neck trauma (J-FAINT) project, IRaq and Afghanistan 2003-2011," Otolaryngol. Head Neck Surg., (2013) 148(3): pp. 403-408.

* cited by examiner

HYDROGEL TISSUE EXPANDERS

PRIORITY STATEMENT

The present invention is a PARK, Kinam et al United States Nationalization of PCT patent application no PCT/US2015/025556, filed 13 Apr. 2014, which is fully incorporated herein by reference; and claims benefit of priority to PARK, Kinam et al U.S. provisional patent application No. 61/979,080, that was filed on 14 Apr. 2014 which is also fully incorporated herein by reference.

Research reported in this patent was partially supported by the National Institute of General Medical Sciences of the National Institutes of Health under Award Number R44GM 106735. The content is solely the responsibility of the inventors and does not necessarily represent the official views of the National Institutes of Health.

This invention was created in the performance of a Cooperative Research and Development Agreement with the Department of Veterans Affairs, an agency of the U.S. Government, which has certain rights in this invention.

FIELD OF INVENTION

The present invention relates to novel, biodegradable, cross-linked hydrogels that are useful as tissue expanders. These hydrogels are biocompatible, self-inflating and membrane-free They swell slowly and elicit minimal tissue response, while allowing for easy manipulation by a medical practitioner at the time of emplacement.

BACKGROUND OF THE INVENTION

Tissue expanders are an important and integral part of reconstructive surgery. They are used to expand and increase the skin, or mucosa, to eventually allow the surgeon to reconstruct lost tissues. S. R. Baker, "*Fundamentals of expanded tissue,*" Head Neck, (1991) 13(4): 327-33. Tissue expanders have been used in the head, face, neck (H. Jhuma, et al., "*Repair of a cheek defect with the tissue expander method: A case report,*" Bull. Tokyo Dent. Coll., (1997) 38(4): pp. 311-316; O. Antonyshyn, et al., "*Tissue expansion in head and neck reconstruction.*" Plast. Reconstr. Surg., (1988) 82(1): pp. 58-68; J. B. Wieslander, "*Tissue expansion in the head and neck: A 6-year review,*" Scand. J. Plast. Reconstr. Surg., (1991) 25(1): pp. 47-56; J. T. Chun and R. J. Rohrich, "*Versatility of tissue expansion in head and neck burn reconstruction,*" Ann. Plast. Surg., (1998) 41(1): pp. 11-16; and S. E. MacLennan, et al., "*Tissue expansion in head and neck burn reconstruction,*" Clin. Plast. Surg., (2000) 27(1): pp. 121-132), chest wall (R. Newman and D. C. Cleveland, "*Three-dimensional reconstruction of ultra-fast chest CT for diagnosis and operative planning in a child with right pneumonectomy syndrome,*" Chest, (1994) 106 (3): pp. 973-974), scapula, shoulder, forearm (V. I. Sharo-baro, et al., "*First experience of endoscopic implantation of tissue expanders in plastic and reconstrucuve surgery,*" Surg. Endosc., (2004) 17(12) p. 513-517), ear (B. S. Bauer, "*The role of tissue expansion in reconstruction of the ear,*" Clin. Plast. Surg., (1990) 17(2): pp. 319-325), finger (R. L. Simpson and M. E. Flaherty, "*The burned small finger,*" Clin. Plast. Surg., (1992) 19(3): pp. 673-682), hairline (R. Silfen, et al., "*Tissue expansion for frontal hairline restoration in severe alopecia in a child,*" Burns, (2000) 26(3): pp. 294-297), lumbosacral, perineum (T. O. Acarturk, et al., "*Reconstruction of difficult wounds with tissue-expanded free flaps,*" Ann. Plast. Surg, (2004) 52(5): pp 493-499; discussion p. 500), foot (P. Rosselli, et al., "*Use of a soft tissue expander before surgical treatment of clubfoot in children and adolescents,*" J. Pediatr. Orthop., (2005) 25(3): pp. 353-356), and calf regions (V. I. Sharobaro, et al., "*First experience of endoscopic implantation of tissue expanders in plastic and reconstructive surgery,*" Surg. Endosc., (2004) 17(12) p. 513-517).

Hydrogel tissue expanders have been developed for use in the resorbed alveolar ridge, cleft palate (K. F. Kobus, "*Cleft palate repair with the use of osmotic expanders: A preliminary report,*" Journal of Plastic, Reconstructive & Aesthetic Surgery, (2007) 60: pp. 414-421), and outside the oral cavity (S. J. Bergé, et al., "*Tissue expansion using osmotically active hydrogel systems for direct closure of the donor defect of the radial forearm flap,*" Plast. Reconstr. Surg., (2001) 108(1): pp. 1-5, discussion pp. 6-7).

Tissue expanders have been used to expand the attached mucosa of the alveolar ridge of resorbed maxillae and mandibles. D. Lew, et al., "*Use of a soft tissue expander in alveolar ridge augmentation: A preliminary report,*" J. Oral Maxillofac. Surg., (1986) 44(7): pp. 516-519; T. M. Hassan, "*Mandibular alveolar ridge augmentation using a soft tissue expander: Report of case,*" J. Conn. State Dent. Assoc., (1988) 62(3): pp. 130-134; D. Lew, et al., "An open procedure for placement of a tissue expander over the atrophic alveolar ridge," J. Oral Maxillofac. Surg., (1988) 46(2): pp. 161-166; A. R. Wittkampf, "*Short-term experience with the subperiosteal tissue expander in reconstruction of the mandibular alveolar ridge.*" J. Oral Maxillofac. Surg., (1989) 47(5): pp. 469-474; A. A. Quayle, et al., "*Alveolar ridge augmentation using a new design of inflatable tissue expander: Surgical technique and preliminary results,*" Br. J. Oral Maxillofac. Surg., (1990) 28(6): pp. 375-382; H. C. Schwartz and R. J. Relle, "*Extraoral placement of a subperiosteal tissue expander for reconstruction with hydroxy-lapatite of the severely atrophic mandibular alveolar ridge,*" J. Oral Maxillofac. Surg., (1990) 48(2): pp. 157-161; D. Lew, et al., "*Use of subperiosteal implants with distal filling ports in the correction of the atrophic alveolar ridge,*" Int. J. Oral Maxillofac. Surg., (1991) 20(1): pp. 15-17; D. J. Zeiter, et al., "*The use of a soft tissue expander in an alveolar bone ridge augmentation for implant placement,*" Int. J. Periodontics Restorative Dent., (1998) 18(4): pp. 403-409; and J. M. Vlassis, et al., "*Controlled subperiosteal tissue expansion to facilitate GBR for the placement of endosseous dental implants,*" Int. J. Periodontics Restorative Dent., (1999) 19(3): pp. 289-297.

Animal studies have supported these clinical reports. K. Tominaga, et al., "*An animal model for subperiosteal tissue expansion,*" J. Oral Maxillofac. Surg., (1993) 51(11): pp. 1244-1249; and M. B. Hürzeler, et al., "*Guided bone regeneration around dental implants in the atrophic alveolar ridge using a bioresorbable barrier: An experimental study in the monkey,*" Clin. Oral Implants Res., (1997) 8(4): pp. 323-331. However, none of these hydrogels can be shaped by the surgeon at the time of surgical insertion.

The Joint Theater Trauma Registry (JTTR) was recently queried for data from United States military injuries from Afghanistan (Operation Enduring Freedom [OEF]) and Iraq (Operation Iraqi Freedom [OIF]) from January 2003 to May 2011. B. A. Feldt, et al., "*The joint facial and invasive neck trauma (J-FAINT) project, Iraq and Afghanistan 2003-2011,*" Otolaryngol. Head Neck Surg., (2013) 148(3): pp. 403-408. Of the 37,523 discrete facial and penetrating neck injuries that occurred in 7177 service members injured, fracture sites occurred in the maxilla (25%) and mandible (21%). Many of these injuries will require dental restorative procedures that will include dental restorations involving dental implants and intraoral bone grafts.

Metal implants are a standard treatment for the replacement of jaws, teeth, ears, noses, and other parts of the face that have been lost from traumatic injury or disease. Placement of metal implants requires bone for stability and ultimate osseo-integration. When teeth are lost, the mandible and maxilla alveolar bone resorb—a natural phenomenon found in almost every patient. When a mandible or maxilla resorbs, there is often not enough bone for the necessary stability of an implant. Often, bone grafts must be used to replace the lost bone before an implant can be placed. A common problem with the surgical placement of any bone graft—e.g., autogenous, allograft, alloplast, etc. . . . —is inadequate soft tissue to close over the bulk of bone graft material.

Presently, the standard of care uses a silicone "balloon" type of tissue expander. This type of tissue expander requires the periodic injection of fluid (usually sterile saline) into a self-sealing valve to increase the volume of this silicone-type tissue expander. A stem with a valve must be made available through the skin or mucosa from the surgical site where the tissue expander is placed. Often the tissue expander must remain in place for weeks to months until the tissue has been expanded to the desired size.

Although newer designs have reduced complications associated with tissue expanders (R. H. Schuster, et al., "*The use of tissue expanders in immediate breast reconstruction following mastectomy for cancer*," Br. J. Plast. Surg., (1990) 43(4): pp. 413-418; S. L. Spear and A. Majidian, "*Immediate breast reconstruction in two stages using textured, integrated-valve tissue expanders and breast implants: A retrospective review of 171 consecutive breast reconstructions from 1989 to 1996*," Plast. Reconstr. Surg., (1998) 101(1): pp. 53-63; and J. J. Disa, et al., "*The premature removal of tissue expanders in breast reconstruction*," Plast. Reconstr. Surg., (1999) 104(6): pp. 1662-1665), a frequent complication with this type of tissue expander is infection about the exposed surgical area (E. K. Manders, et al., "*Soft-tissue expansion: Concepts and complications*," Plast. Reconstr. Surg., (1984) 74(4): pp. 493-507; J. B. McCraw, et al., "*An early appraisal of the methods of tissue expansion and the transverse rectus abdominis musculocutaneous flap in reconstruction of the breast following mastectomy*," Ann. Plast. Surg., (1987) 18(2): pp. 93-113; J. Gibney, "*The long-term results of tissue expansion for breast reconstruction*," Clin. Plast. Surg., (1987) 14(3): pp. 509-518; J. D. Holmes, "*Capsular contracture after breast reconstruction with tissue expansion*," Br. J. Plast. Surg., (1989) 42(5): pp. 591-594; R. H. Schuster, et al., "*The use of tissue expanders in immediate breast reconstruction following mastectomy for cancer*," Br. J. Plast Surg., (1990) 43(4): pp. 413-418; and G. P. Pisarski, et al., "*Tissue expander complications in the pediatric burn patient*," Plast. Reconstr. Surg., (1998) 102(4): pp. 1008-1012). Moreover, surgical techniques are often modified to accommodate the danger of rupture and bleeding from a tissue expander surgical site. V. I. Sharobaro, et al., "*First experience of endoscopic implantation of tissue expanders in plastic and reconstructive surgery*," Surg. Endosc., (2004) 17(12): p. 513-517.

An alternative to tissue expanders to effectively cover bone grafts are surgical techniques which avoid necrosis of the soft-tissue flap covering a bone graft. Tension release of the periosteum, avoidance of the muscles in the flap, and, to a lesser extent, vertical releasing incisions are the primary techniques used in clinical practice. G. Greenstein, et al., "*Flap advancement: practical techniques to attain tension-free primary closure*," J. Periodontol, (2009) 80(1): pp. 4-15. Frequently, the oral mucosa used to surgically cover the bone graft dies at the periphery and exposes the graft to all the microbes of the oral cavity, often resulting in loss or partial-loss of the graft. W. Mörmann and S. G. Ciancio, "*Blood supply of human gingiva following periodontal surgery. Afluorescein angiographic study*," J. Periodontol, (1977) 48(11): pp. 681-692; and T. N. McLean, et al., "*Vascular changes following mucoperiosteal flap surgery: A fluorescein angiography study in dogs*," J. Periodontol, (1995) 66(3): pp. 205-210. Extra soft tissue (skin or mucosa) created by a tissue expander to cover any graft material would provide a significant improvement in clinical therapy.

WO 2007016371 A3 entitled "*Readily shapeable xerogels having controllably delayed swelling properties*" describes reshapable xerogels with mechanically soft properties. However, Applicants of the present application have made substantial advancements to the technology based on subsequent in vitro and in vivo studies. The novel hydrogel implants of the present invention address a number of problems associated with prior designs. For example, they:

a. are membrane-free and self-swelling;
b. are comprised of non-toxic, biocompatible components;
c. exhibit delayed swelling, so as not to rupture an unhealed incision after emplacement;
d. exhibit controlled swelling, without falling apart, to a maximum size which is less than traditional hydrogels;
e. are elastic when dry, and moldable by a medical practitioner into a smooth shape without sharp edges, which can damage tissue; and
are robust enough to stay intact throughout the tissue expansion procedure.

SUMMARY OF THE INVENTION

The present invention provides tissue expanders comprising biodegradable, chemically-cross-linked hydrogels which are elastic in the dry state. These biocompatible tissue expanders are self-inflating and membrane-free. They swell slowly and elicit minimal negative tissue responses, while allowing for rapid and easy manipulation by the surgeon at the time of emplacement.

In a $1^{st}$ aspect, the present invention provides a hydrogel, chemically-cross-linked via ester-acrylate bonds, comprising: triblock $(PLGA)_x$-$(PEG)_y$-$(PLGA)_z$ copolymers having molecular weights of 1,000 to 50,000 Da, wherein:

the percent ratio of ((molecular weight of total PLGA)/(molecular weight of total copolymer)×100%) for the copolymers is >60%; and each of x, y, and z is independently an integer from 1 to 500.

In a $1^{st}$ embodiment, the triblock $(PLGA)_x$-$(PEG)_y$-$(PLGA)_z$ copolymers have molecular weights of 2,000 to 40,000 Da.

In a preferred embodiment, the triblock $(PLGA)_x$-$(PEG)_y$-$(PLGA)_z$ copolymers have molecular weights of 5,000 to 20,000 Da.

In a $2^{nd}$ embodiment, the percent ratio of ((molecular weight of total PLGA)/(molecular weight of total copolymer)×100%) for the copolymers is 95% to 75%.

In a preferred embodiment, the percent ratio of ((molecular weight of total PLGA)/(molecular weight of total copolymer)×100%) for the copolymers is 95% to 85%.

In a $3^{rd}$ embodiment, the triblock $(PLGA)_x$-$(PEG)_y$-$(PLGA)_z$ copolymers comprise 1% to 80% (w/w) of the hydrogel.

In a preferred embodiment, the triblock $(PLGA)_x$-$(PEG)_y$-$(PLGA)_z$ copolymers comprise 20% to 70% (w/w) of the hydrogel.

In a more preferred embodiment, the triblock $(PLGA)_x$-$(PEG)_y$-$(PLGA)_z$ copolymers comprise 30% to 60% (w/w) of the hydrogel.

In a 4$^{th}$ embodiment, the hydrogel further comprises (PLGA)- or (PLA)-diacrylates having molecular weights of 1,000 to 200,000 Da.

In a preferred embodiment, the (PLGA)- or (PLA)-diacrylates have molecular weights of 2,500 to 150,000 Da.

In a more preferred embodiment, the (PLGA)- or (PLA)-diacrylates have molecular weights of 5,000 to 100,000 Da.

In another preferred embodiment, the concentration of the (PLGA)- or (PLA)-diacrylates is 1% to 30% (w/w) of the hydrogel.

In a more preferred embodiment, the concentration of the (PLGA)- or (PLA)-diacrylates is 2% to 25% (w/w) of the hydrogel.

In a most preferred embodiment, the concentration of the (PLGA)- or (PLA)-diacrylates is 3% to 20% (w/w) of the hydrogel.

In another preferred embodiment, the lactide:glycolide ratio in the (PLGA)-diacrylate copolymer ranges from about 50:50 to about 99:1.

In a more preferred embodiment, the lactide:glycolide ratio in the (PLGA)-diacrylate copolymer is about 50:50.

In a 5$^{th}$ embodiment, the hydrogel further comprises poly(ethylene glycol) diacrylates having molecular weights of 100 to 10,000 Da.

In a preferred embodiment, the poly(ethylene glycol) diacrylates have molecular weights of 300 to 5,000 Da.

In a more preferred embodiment, the poly(ethylene glycol) diacrylates have molecular weights of 500 to 1,000 Da.

In another preferred embodiment, the concentration of the poly(ethylene glycol) diacrylates is 5% to 70% (w/w) of the hydrogel.

In a more preferred embodiment, the concentration of the poly(ethylene glycol) diacrylates is 10% to 60% (w/w) of the hydrogel.

In a most preferred embodiment, the concentration of the poly(ethylene glycol) diacrylates is 15% to 55% (w/w) of the hydrogel.

In a 6$^{th}$ embodiment, the hydrogel further comprises ethylene glycol dimethacrylate as a crosslinker.

In a preferred embodiment, the ethylene glycol dimethacrylate has a concentration of 1% to 30% (w/w) of the hydrogel.

In a more preferred embodiment, the ethylene glycol dimethacrylate has a concentration of 3% to 20% (w/w) of the hydrogel.

In a most preferred embodiment, the ethylene glycol dimethacrylate has a concentration of 5% to 20% (w/w) of the hydrogel.

In a 7$^{th}$ embodiment, the cross-linking density (trilinked chains/mg) of the hydrogel is 0.1 to 5.0.

In a preferred embodiment, the cross-linking density is 0.5 to 4.0.

In a more preferred embodiment, the cross-linking density is 1.0 to 3.0.

In an 8$^{th}$ embodiment, the overall hydrophobicity (directly water insoluble content/water soluble content) of the hydrogel is 20% to 100%.

In a preferred embodiment, the overall hydrophobicity is 30% to 95%.

In a more preferred embodiment, the overall hydrophobicity is 40% to 90%.

In a 9$^{th}$ embodiment, $(PLGA)_x$ is about 1000 to about 7000 Da, $(PEG)_y$ is about 200 to about 2000 Da, and $(PLGA)_z$ is about 1000 to about 7000 Da.

In a preferred embodiment, $(PLGA)_x$ is about 3000 to about 5500 Da.

In another preferred embodiment, $(PLGA)_z$ is about 3000 to about 5500 Da.

In another preferred embodiment, $(PEG)_y$ is about 500 to about 1500 Da.

In another preferred embodiment, $x=z$.

In a 10$^{th}$ embodiment, the lactide:glycolide ratio in the (PLGA)x copolymer ranges from about 50:50 to about 99:1.

In a preferred embodiment, the lactide:glycolide ratio in the (PLGA)x copolymer is about 50:50.

In an 11$^{th}$ embodiment, the lactide:glycolide ratio in the (PLGA)z copolymer ranges from about 50:50 to about 99:1.

In a preferred embodiment, the lactide:glycolide ratio in the (PLGA)z copolymer is about 50:50.

In a 12$^{th}$ embodiment, the hydrogel is impregnated with one or more drugs selected from: a growth factor, an antibiotic, a pain-relieving drug, a blood-coagulation modifying agent, and an immune-response modifying agent.

In a preferred embodiment, the growth factor is a bone-morphogenic protein, Epidermal growth factor, Transforming growth factor, Hepatocyte growth factor, Vascular endothelial growth factor, Platelet derived growth factor, Fibroblast growth factor, Keratinocyte growth factor, or cytokine.

In another preferred embodiment, the antibiotic is a tetracycline, a beta-lactamase inhibitor, penicillin, or cephalosporin.

In another preferred embodiment, the pain-relieving drug is an aminoamide-class or aminoester-class anesthetic, non-steroidal anti-inflammatory drug, or steroidal anti-inflammatory drug.

In a more preferred embodiment, the pain-relieving drug is lidocaine or benzocaine.

In another preferred embodiment, the blood-coagulation modifying agent is warfarin, heparin or thrombin.

In another preferred embodiment, the immune-response modifying agent is everolimus, a non-steroidal anti-inflammatory drug, or a steroidal anti-inflammatory drug.

In a 2$^{nd}$ aspect, the invention provides a method for facilitating soft tissue, skin, or mucosal tissue expansion comprising the steps:

a) implanting a tissue expander beneath a target locus of soft tissue, skin, or mucosal tissue sought to be expanded, the tissue expander comprising: a hydrogel, chemically-cross-linked via ester-acrylate bonds, comprising: triblock $(PLGA)_x$-$(PEG)_y$-$(PLGA)_z$ copolymers having molecular weights of 1,000 to 50,000 Da, wherein: the percent ratio of ((molecular weight of total PLGA)/(molecular weight of total copolymer)×100%) for the copolymers is >60%, and each of x, y, and z is independently an integer from 1 to 500; and b) allowing the tissue expander to expand naturally beneath the tissue.

In a 1$^{th}$ embodiment, the 1-day swelling ratio (Wt/Wd at 1-day) of the hydrogel is 100% to 500%.

In a preferred embodiment, the 1-day swelling ratio is 100% to 300%.

In a more preferred embodiment, the 1-day swelling ratio is 100% to 200%.

In a 2$^{nd}$ embodiment, the final swelling ratio (Wt/Wd at >40 days) of the hydrogel is 100% to 700%.

In a preferred embodiment, the final swelling ratio is 150% to 500%.

In a more preferred embodiment, the final swelling ratio is 200% to 400%.

In a 3$^{rd}$ embodiment, the modulus of elasticity of the hydrogel is 0.1 to 100 kPa.

In a preferred embodiment, the modulus of elasticity is 0.5 to 50 kPa.

In a more preferred embodiment, the modulus of elasticity is 1 to 25 kPa.

In a 4$^{th}$ embodiment, the hydrogel has a semi-cylindrical shape with a rounded tip to aid in clinical implantation.

In 5$^{th}$ embodiment, the mucosal tissue expansion is selected from ridge augmentation, cleft palate repair, and in-utero cleft palate repair.

In a 6$^{th}$ embodiment, the ridge augmentation is in response to trauma to the jaw or bone resorption post-tooth removal.

In 7$^{th}$ embodiment, the cleft palate repair is in response to a congenital defect, wherein the repair is optionally performed post-partum or in-utero.

In an 8$^{th}$ embodiment, the skin expansion application is in response to hair transplantation, or skin grafting applications due to trauma wounds, burns, congenital defects, or surgical procedure.

In a 9$^{th}$ embodiment, the skin expansion application is in response to aesthetic requirements of breast augmentation or a transgender procedure.

In a 10$^{th}$, the expansion applications is applied to reconstructive surgery.

In an 11$^{th}$ embodiment, the method further comprises the step of (between steps a) and b)): closing the incision.

In a 12$^{th}$ embodiment, the method further comprises the step of: c) surgically removing the tissue expander.

In a 13$^{rd}$ embodiment, the method further comprises the step of: c) allowing the tissue expander to decompose naturally in vivo.

For illustration purposes, the hydrogels of the invention can be used as tissue expanders applied to military veterans who have suffered facial trauma due to war-related injuries. Ridge augmentation can be utilized in order to allow for implantation of a permanent tooth implant to return oral aesthetic and functionality.

In a 3$^{th}$ aspect, the present invention provides triblock $(PLGA)_x$-$(PEG)_y$-$(PLGA)_z$ copolymers having molecular weights of 1,000 to 50,000 Da, wherein: the percent ratio of ((molecular weight of total PLGA)/(molecular weight of total copolymer)×100% for the copolymers is >60%; and each of x, y, and z is independently an integer from 1 to 500.

It will be appreciated that all allowable combinations of the above aspects/embodiments, as well as other aspects/embodiments disclosed elsewhere herein, are contemplated as additional aspects/embodiments of the invention.

DETAILED DESCRIPTION OF THE INVENTION

Figure 1:
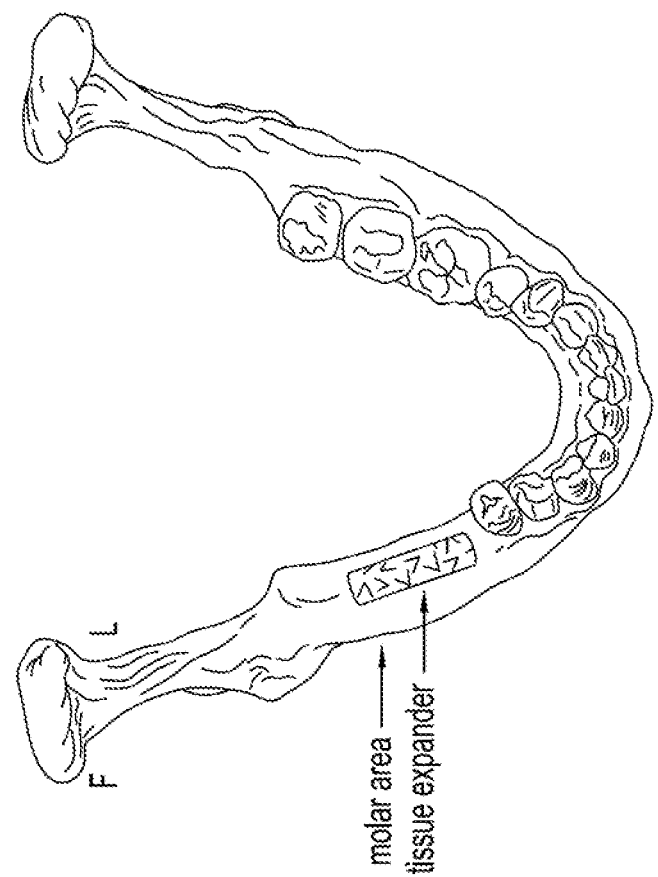
FIG. 1 illustrates the use of a tissue expander in the mandibular or area, but it could also be used in the anterior and maxilla alveolar areas.
Figure 1:
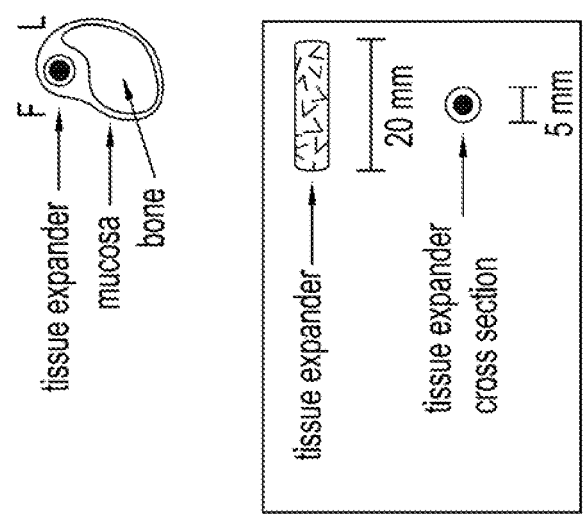

The present invention provides tissue expanders comprising novel hydrogels which elicit controlled expansion of mucosa or skin following surgical implantation. These expanders can be reshaped by the surgeon prior to emplantation without losing their characteristic of delayed expansion. For dental purposes, these hydrogel tissue expanders are typically placed in a resorbed alveolar ridge. FIG. 1 illustrates the use of a tissue expander in the mandibular posterior area, but it could also be used in the anterior and maxilla alveolar areas. Outside the oral cavity, the device can be used to expand the skin in a variety of locations.

The hydrogel expanders of the present invention add a very useful feature to tissue expanders: the ability to modify the size and shape of the implant. These devices are useful in many areas of reconstructive surgery, since they can assume a wide range of large to very small sizes and shapes. Beyond intraoral and plastic surgical procedures, these devices can be used for in utero closure of conditions such as spinae bifida (T. Kohl, "*Minimally invasive feloscopic interventions: An overview in* 2010," Surg. Endosc., (2010) 24(8): pp. 2056-2067; N. S. Adzick, et al., "*A randomized trial of prenatal versus postnatal repair of myelomeningocele*," N. Engl. J. Med., (2011) 364(11): pp. 993-1004; and M. A. Fichter, et al., "*Fetal spina bifida repair*—current trends and prospects of intrauterine neurosurgery," Fetal Diagn. Ther., (2008) 23(4): pp. 271-286), cleft lips and palates, especially using conventional and feto-endoscopic surgery (N. A. Papadopulos, et al., "*Foetal surgery and cleft lip and palate: Current status and new perspectives*," Br. J. Plast. Surg., (2005) 58(5): pp. 593-607), as well as other in utero surgical procedures (T. Kohl, "*Minimally invasive fetoscopic interventions: An overview in* 2010," Surg. Endosc., (2010) 24(8): pp. 2056-2067).

As used herein:

"AIBN" means azobisisobutyronitrile;

"-DA" indicates that a material has been diacrylated;

"DCM" means dichloromethane;

"DCS" means differential scanning calorimetry;

"-DMA" indicates methacrylation of a material;

"DMSO" means dimethylsulfoxide;

"EGDMA" means ethylene glycol dimethacrylate;

"Ether" means diethyl ether;

"ETO" means ethylene oxide;

"MW" means molecular weight;

"PEG" means polyethylene glycol;

"PLA" means polylactic acid;

"PLGA" means poly(lactic-co-glycolic acid);

"RG503-DA" indicates the acrylated form of commercially-obtained PLGA;

"RT" means room temperature; and

"TEA" means triethylamine;

The following preparations, Examples and tests illustrate how to make and use specific embodiments of the invention, and are not intended to limit the scope thereof:

Preparations:

Triblock Copolymer Synthesis:

$(PLGA)_x$-$(PEG)_y$-$(PLGA)_z$ triblock copolymers are synthesized by ring opening reaction, with PEG diol used as an initiator. A desired block size of PEG-diol is commercially purchased and purified by dissolution in DCM and precipitation in ether. Afterwards, a specific quantity is dried by heating to 150° C. under a deep vacuum in a 2-neck round-bottom flask for three hours. Commercially purchased lactide and glycolide monomers are recrystallized twice in ethyl acetate to further purify. Prior to use, stannous octoate $(Sn(OCt)_2)$ is vacuum distilled to remove residual water, and stored over desiccant. A predetermined molar quantity of these monomers is added to the PEG and $Sn(OCt)_2$ catalyst dissolved in toluene (10% w/v). These are placed under a deep vacuum for 0.5 hour, and then heated to 150° C. for 8 hours. After synthesis, the $(PLGA)_x$-$(PEG)_y$-$(PLGA)_z$ triblock polymer is dissolved in a small amount of DCM, filtered, and re-precipitated in ether.

In a typical PLGA synthesis, the presence of small quantities of water, along with the $Sn(Oct)_2$, initiate the ring opening reaction. In this reaction, the $Sn(Oct)_2$ catalyst converts the alcohol endcaps of the polyethylene glycol to an activated —RO-Sn+ form, which causes these sites to serve for initiation of the PLGA chain, thus leading to a block copolymer.

TABLE 1 describes several Examples of triblock $(PLGA)_x$-$(PEG)_y$-$(PLGA)_z$ copolymers. Because these triblock copolymers are not commercially available at the listed molecular weights, they are custom synthesized. Of these triblocks, TB05 notably has biodegradable block lengths which are substantially higher in molecular weight than the original PEG block (10:1 ratio of PLGA:PEG). This renders the macromer inherently water insoluble even prior to cross-linking. The application of this macromer, and others like it, to the generation of hydrogels lends itself to surprising changes in the resultant gel properties.

TABLE 1

Triblock $(PLGA)_x$-$(PEG)_y$-$(PLGA)_z$ copolymers

| Name | PEG Block (Nominal MW) | LA:GA Ratio | PLGA Block (Nominal MW) |
|---|---|---|---|
| TB01 | 1,500 | 1:1 | 333 |
| TB02 | 1,500 | 4:1 | 246 |
| TB03 | 2,000 | 1:0 | 750 |
| TB04 | 2,000 | 1:1 | 666 |
| TB05 | 1,000 | 1:1 | 5,000 |
| TB06 | 1,500 | 4:1 | 492 |
| TB07 | 1,500 | 1:1 | 340 |
| TB08 | 400 | 1:1 | 717 |
| TB09 | 1000 | 1:1 | 7500 |
| TB10 | 1000 | 1:1 | 3500 |
| TB11 | 1000 | 1:0 | 5000 |

Triblock Copolymer Acrylation:

Following synthesis and purification of the triblock $(PLGA)_x$-$(PEG)_y$-$(PLGA)_z$ copolymer, the resultant polymer is activated with acrylate endcaps to allow cross-linking. A two-neck flask is purged with dry nitrogen for 20-30 min. The triblock $(PLGA)_x$-$(PEG)_y$-$(PLGA)_z$ copolymer is dissolved in 30 ml of benzene or DCM. TEA and acryloyl chloride are added to the reaction flask in a molar ratio of 3-times the (—OH) groups, and the reaction mixture is stirred at 80° C. for 3 h under reflux conditions. The reaction mixture is then filtered to remove triethylamine hydrochloride, and the filtrate is dropped into excess n-hexane to precipitate the DA-$(PLGA)_x$-$(PEG)_y$-$(PLGA)_z$-DA product.

Subsequently, this product is re-dissolved in DMSO to a concentration of approximately 20% w/v, and reprecipitated in ethanol. This secondary process eliminates the excess acrylic acid formed from acryloyl chloride side reactions. Alternatively, the product is dissolved in ethyl acetate and mixed with activated carbon for 24 hours, followed by filtration, rotary evaporation (to remove ethyl acetate), re-dissolution in DCM, and precipitation in either ether or hexane:ethanol (80:20) mix. Finally, the precipitated product is dried at room temperature under reduced pressure for 24 h.

Figure 2:
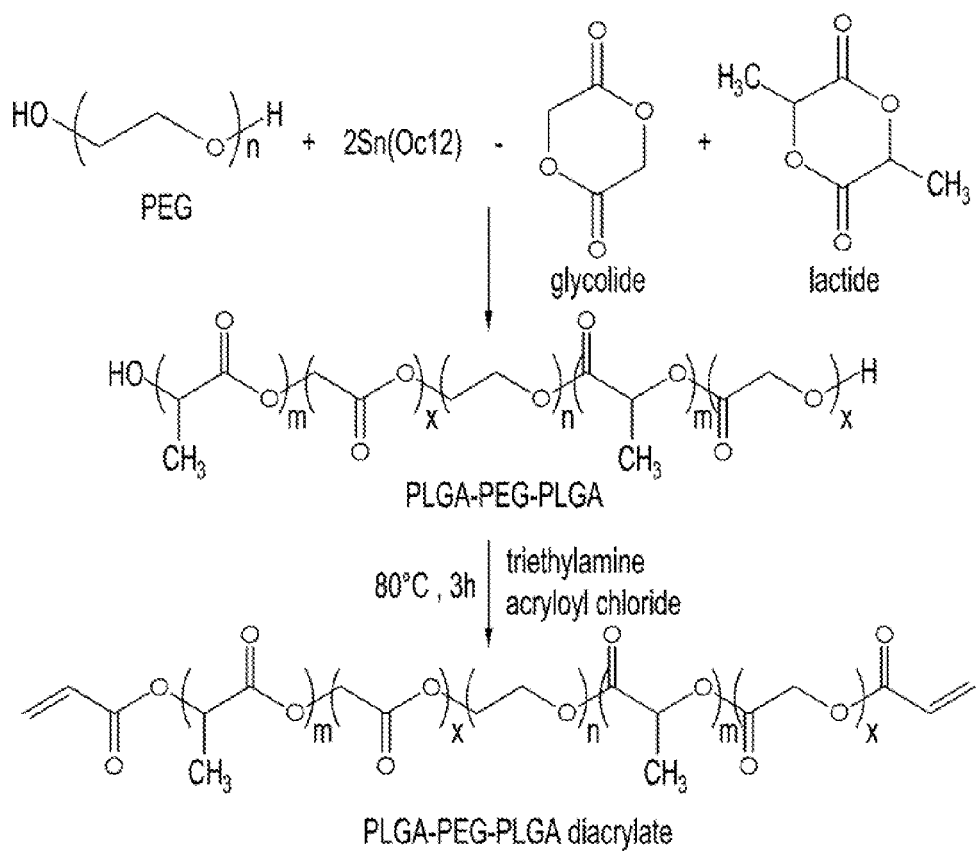
FIG. 2 shows the schematic chemical reaction process.
Figure 3:
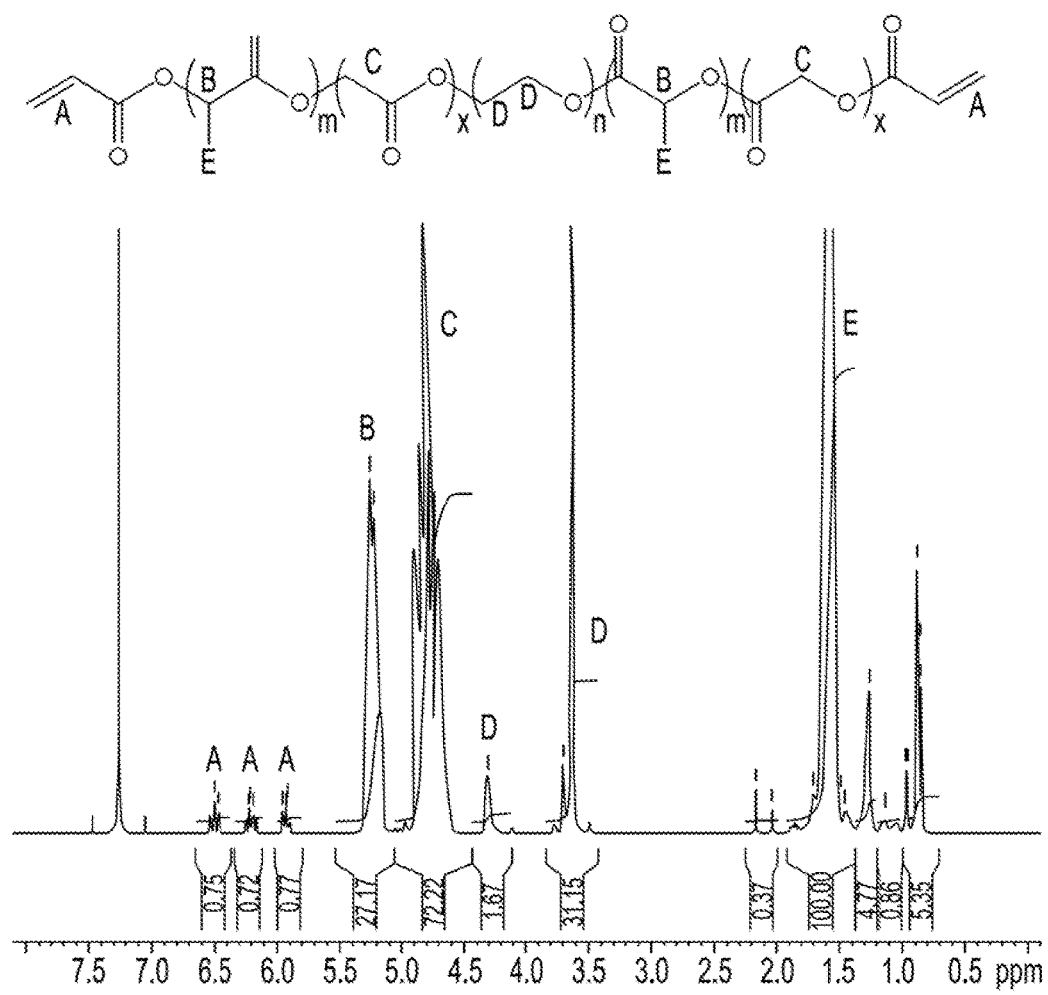
FIG. 3 shows HNMR characterization results for TB05-DA, with the indicated peak assignments confirming successful triblock synthesis and diacrylation.

FIG. 2 shows the schematic chemical reaction process. FIG. 3 shows HNMR characterization results for TB05-DA, with the indicated peak assignments confirming successful triblock synthesis and diacrylation. The addition of the acrylate group renders the polymer vinylically-active, allowing it to participate in radical-chain, cross-linking reactions, thus converting the material to a "macromer."

PLGA/PLA Acrylation:

A similar process as described for the triblock copolymer is utilized to acrylate PLGA. For this process, either a commercially-sourced PLGA may be utilized (e.g. Resomer RG503H MW ~25,000 Da, Mn ~12,000 Da acid end-capped), which results in single-end acrylation, or a custom-synthesized PLGA/PLA-diacrylate may be generated. For the synthesis of PLGA/PLA-diacrylate, the polyester is synthesized utilizing 1,10-decanediol as the precursor. The 1,10-decanediol is briefly purged at RT under deep vacuum to remove any surface moisture, and predetermined molar quantities of lactide, glycolide and $Sn(Oct)_2$ initiator are added to the decanediol, followed by vacuum purging and heating at 150° C. for 8 hours.

Prior to acrylation, the polyester is dissolved in dichloromethane and re-precipitated in hexane to purify it. The PLGA or PLA thus formed is di-alcohol end-capped, allowing for attachment of acrylate units on both termini of the polyester. After purification, the polyester is redissolved in DCM and reacted with 3× (—OH) molar equivalent of TEA and acryloyl chloride, and purified, as described above.

For the custom synthesized materials, the compositions are named as in following example: "PLGA(1:1, 10,000 Da)-DA". The di-alcohol end-capped polyester allows for not only additional hydrophobicity of the molecule, but also cross-linking, as the subsequent diacrylated polyester can conjugate two chains together.

Methacrylation:

The process of methacrylation is die same as that described for acrylation, with the exception that methacryloyl chloride is utilized during the reaction instead of acryloyl chloride.

Hydrogel Formation:

The components $(PLGA)_x$-$(PEG)_y$-$(PLGA)z$ diacrylate, PLGA diacrylate, ethylene glycol dimethacrylate (EGDMA) and commercially-purchased PEG diacrylate, as well as other additives including commercial monomers and cross-linkers, are combined in DMSO (anhydrous) solvent to a total concentration of 10% to 30% w/v solid/DMSO. AIBN is recrystallized from methanol prior to use, while the other components are used as received, or as generated. AIBN is added to the DMSO at a concentration of ~0.35% w/w solids, and the solution is briefly sparged with inert gas to remove dissolved oxygen. The solution is then placed in a 65° C. oven overnight. T. H. Tran, et al., "*Biodegradable Elastic Hydrogels for Tissue Expander Application*," Handbook of Biodegradable Polymers, (2011) 9: p. 2.

The solution undergoes radical cross-linking reaction to form a three-dimensional hydrogel network. This is visually confirmed upon removal from the oven, as the solution solidifies due to cross-linking. The resultant hydrogels are immersed in alternating solutions of ethanol and ethyl acetate to remove unreacted residues and DMSO over the course of 1-2 weeks. The hydrogels are subsequently dried in a vacuum oven for more than 24 h.

Successful synthesis of the hydrogel is further confirmed by FTIR. Upon triblock formation a peak, additional to the spectra of the PEG precursor, arises around 1750 cm$^{-1}$, corresponding to the formation of the ester carbonyl bonds (C=O). After acrylation, a relatively weak peak is observed at ~650 cmcm$^{-1}$ due to =C—H bending. Upon hydrogel formation, this peak disappears, indicating radical chain polymerization, which consumes the alkene bonds as part of the reaction.

Figure 4:
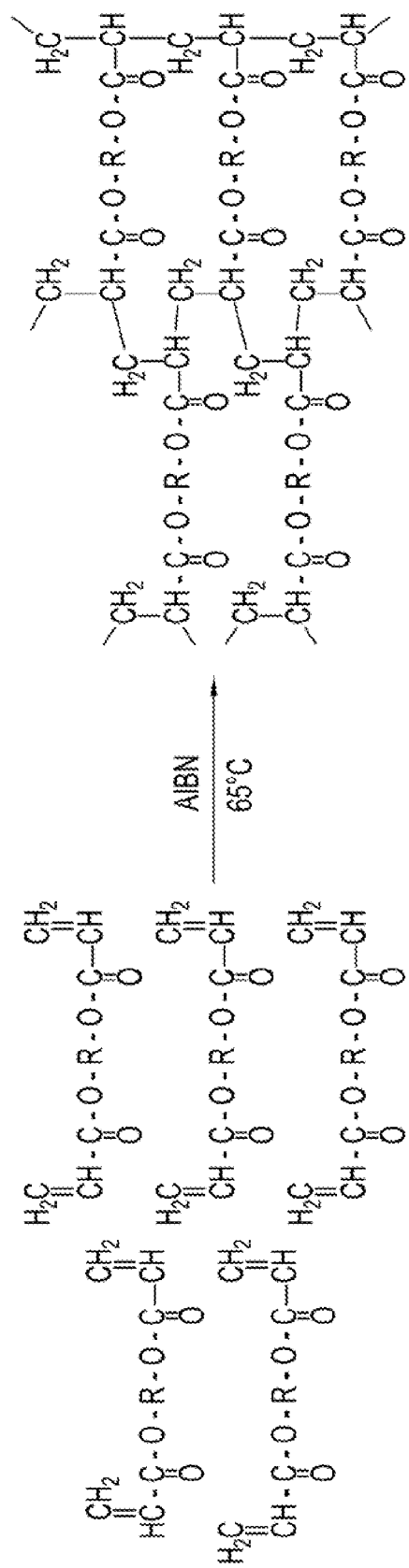
FIG. 4 shows a schematic example of the cross-linking reaction, as described in the section below on Hydrogel Formation.

Further confirmation is obtained by DSC. The PEG precursor exhibits a melting endotherm, typically in the range of 50-60° C., with the resultant triblock showing a melting endotherm slightly lower than the original PEG block, due to block copolymerization. After cross-linking, no melting endotherm is observed below 100° C. (maximum tested temperature), indicating successful formation of a cross-linked polymer, which is thermoset and does not melt upon increasing temperature. The Examples subsequently listed are hydrogels formed by this method. FIG. 4 shows a schematic example of this cross-linking reaction.

In-Vitro Analysis of Hydrogels

Mechanical:

Cylindrical portions of formed hydrogels are cut and their cross-sectional area measured. These hydrogel portions are then loaded onto a mechanical testing device (The TA XTPlus Texture Analyzer from Texture Technologies Corp., Algonquin, Ill.), compressed with a ½-inch radius Dacron tip at a crosshead speed of 0.5 mm/sec to 20% strain, and held there for 60 seconds before the tip is withdrawn. The slope of the stress-strain curve for 2% strain is measured as the "elasticity modulus." The compression force at 20% strain after holding for 60 seconds is divided by the initial compressive force at 20% strain and converted to a percent, to yield "stress relaxation."

The post-degradation mechanical strength of the degraded hydrogels is determined by compressing a sample with a ¼-inch steel ball at a crosshead speed of 0.5 mm/sec. The force at which the hydrogel fails is divided by the height of the hydrogel to obtain "mechanical strength" in N/mm. The higher this number, the stronger the post-degraded hydrogel.

Swelling Rate:

Swelling studies are performed by measuring the "swelling ratio," which is the weight of a swollen gel ($W_s$) divided by the weight of a dry gel ($W_d$). Sample hydrogels are placed in phosphate buffered saline, and the increase in weight due to swelling in water is measured at pre-determined time points after removing excess water with a KIMWIPE® paper.

Swelling Pressure:

The swelling pressure of a hydrogel is measured by placing a cylindrical sample in a mechanical-testing texture analyzer with a specially modified stage. The standard texture analyzer base is replaced with a 37° C. hot plate to allow incubation during measurements. A 22-ml scintillation vial is placed on the base and the dry hydrogel introduced in this vial. The texture analyzer tip (½ inch Dacron) is lowered until it touched the hydrogel. The tip is held still at this position while 10 ml of 0.154 M hydrochloric acid (HCl) is added to the vial, and the tip is held in place for 24 hours while the hydrogel is allowed to swell. HCl is used in the same ionic concentration as bodily fluids, so that PLGA degradation can be expedited with minimal impact on swelling properties. The maximum force exerted by the hydrogel during this time (for all samples this occurred prior to 24 hours) is recorded and divided by the contact area of the swollen hydrogel. This indicates the maximum possible force that the hydrogels can generate by their own swelling power.

Examples 1-19

TABLE 2 lists the compositions of hydrogel Examples 1-16. The formulas include the components listed as % w/v in DMSO. Unless otherwise specified, the PEG-DA has a molecular weight of 700 Da, and the reaction is initiated with 0.35% (w/w solids) AIBN.

TABLE 2

Formulas of hydrogel Examples 1-16

| Example | Formula (% w/v in DMSO) |
|---|---|
| 1 | 10% TB01DA |
| 2 | 7.5% TB01DA; 2.5% PEGDA |
| 3 | 5% TB01DA; 5% PEGDA |
| 4 | 2.5% TB01DA; 7.5% PEGDA |
| 5 | 7.5% TB02DA; 2.5% PEGDA |
| 6 | 5% TB02DA; 5% PEGDA |
| 7 | 2.5% TB02DA; 7.5% PEGDA |
| 8 | 5% TB05DA; 5% PEGDA; 0.01% acrylic acid |
| 9 | 10% TB02DA; 5% PEGDA |
| 10 | 10% TB04DA; 5% PEGDA |
| 11 | 7.5% TB04DA; 7.5% PEGDA |
| 12 | 10% TB04DA; 5% PEGDA; 0.45% acrylic acid |
| 13 | 7.5% TB05DA; 7.5% PEGDA; 0.15% acrylic acid |
| 14 | 7.5% TB02DA; 7.5% PEGDA; 0.15% methylene bisacrylamide; 0.3% acrylic acid |
| 15 | 10% TB06DA; 5% PEGDA; 0.01% ethylene glycol dimethacrylate |
| 16 | 7.5% TB01DA; 7.5% PEGDA; 0.15% PLGADA |

Examples 1-16 are analyzed as described above and their properties listed in TABLE 3. The columns indicate values as shown:

(1) "Initial swelling" is the swelling ratio after the first 24 hours of incubation.

(2) "Maximum swelling" is the highest swelling ratio obtained over the course of the entire experiment (typically 60 days).

(3) "Max time" is the time in days it took to reach the maximum swelling.

(4) "Elasticity" and "stress relaxation" of dry hydrogels indicate their ability to be reshaped.

(5) "Swelling pressure" is in mm Hg and tested as indicated previously.

(6) "Post condition" describes the hydrogel morphology with failure strength in N/mm listed in parenthesis. "ND" indicates that no data is available for the sample for this category.

TABLE 3

Properties of hydrogel Examples 1-16

| Example | Initial Swelling | Maximum Swelling | Max Time (Days) | Elasticity (kPa)/Stress Relaxation (%) | Swelling Pressure (mmHg) | Post Condition (N/mm) |
|---|---|---|---|---|---|---|
| 1 | 5 | 60 | 6 | 5.2/95 | 700 | Liquid |
| 2 | 8 | 138 | 5 | 2.6/92 | 471 | Liquid |
| 3 | 8 | 130 | 14 | 2.0/94 | 450 | Liquid |
| 4 | 11 | 248 | 9 | 2.6/95 | 411 | Liquid |
| 5 | 11 | 81 | 13 | 2.0/96 | 419 | Liquid |
| 6 | 12 | 65 | 24 | 3.0/95 | 433 | Liquid |
| 7 | 12 | 88 | 35 | 2.3/93 | 491 | Liquid |
| 8 | 4 | 11 | 16 | ND/ND | 87 | Liquid |
| 9 | 4 | 8 | 16 | 2.3/94 | >1,000 | Solid (0.05) |
| 10 | 7 | 11 | 8 | 1.04/89 | ND | Solid (ND) |
| 11 | 6 | 9 | 57 | 1.5/90 | ND | Solid (0.04) |
| 12 | 7 | 13 | 16 | 0.68/80 | 728 | Liquid |
| 13 | 2 | 6 | 31 | 0.8/32 | ND | Solid (0.11) |
| 14 | 4 | 5 | 35 | 0.3/47 | ND | Solid (0.49) |
| 15 | 4 | 8 | 17 | 2.0/95 | 1,614 | Solid (0.05) |
| 16 | 1.9 | 2.1 | 17 | 3.1/8.8 | ND | Solid (0.33) |

This series of tests indicates some common results. Generally, hydrogels prepared using these method and materials have the ability to be reshaped using common sharp surgical instruments. Also, these hydrogels have sufficient pressure to expand tissue. Previous researchers had suggested required pressures in the range of 25 to 235 mm Hg. S. J. Bergé, et al., "*Tissue expansion using osmotically active hydrogel systems for direct closure of the donor defect of the radial forearm flap*," Plast. Reconstr. Surg. (2001) 108(1): pp. 1-5, discussion pp. 6-7; K. G. Wiese, "*Tissue expander inflating due to osmotic driving forces of a shaped body of hydrogel and an aqueous solution*," U.S. Pat. No. 5,496,368; and H. S. Z. Min and P. Svedman, "*On expander pressure and skin blood flow during tissue expansion in the pig*," Annals of Plastic Surgery (1988) 21(2): p. 6. Since the expansion of the hydrogels of the present invention is controlled by time instead of pressure, having a maximal obtainable pressure within this range is not an issue. The important point of measuring the maximal pressure is to ensure that the hydrogels have sufficient pressure to expand skin. Adjusting the recipe has its most dramatic impact on the swelling profile of the expander and the strength of the material when expansion is completed. This information led to the preparation of improved device materials in Examples in 17-19.

Example 17

This hydrogel is prepared by reacting a 10% TB05-DA, 5% PEGDA, and 0.75% RG503-DA (w/v) solution in DMSO.

Example 18

This hydrogel is prepared by reacting a 10%, 4 TB05-DA, 5% PEGDA, 0.75% RG503-DA (w/v), and 0.15% ethylene glycol dimethacrylate solution in DMSO.

Example 19

This hydrogel is prepared by reacting a 10% TB05-DA, 5% PEGDA, and 1.5% RG503-DA (w/v) solution in DMSO.

Analysis of Examples 17-19 is focused on the swelling profiles of these hydrogels, both as made and after sterilization via ethylene oxide at 54° C. for a 16 hour cycle. Sterilization by ETO increases the speed of expansion, likely due to some damage of the PLGA chains. This is despite the fact that generally ETO is acknowledged as one of the least damaging methods of sterilization. S. E. Moioli, et al., "*Sustained release of TGFbeta3 from PLGA microspheres and its effect on early osteogenic differentiation of human mesenchymal stem cells*." Tissue Engineering (2006) 12(3): pp. 537-546. The addition of PLGA slows the expansion back down to a reasonable rate.

Figure 5:
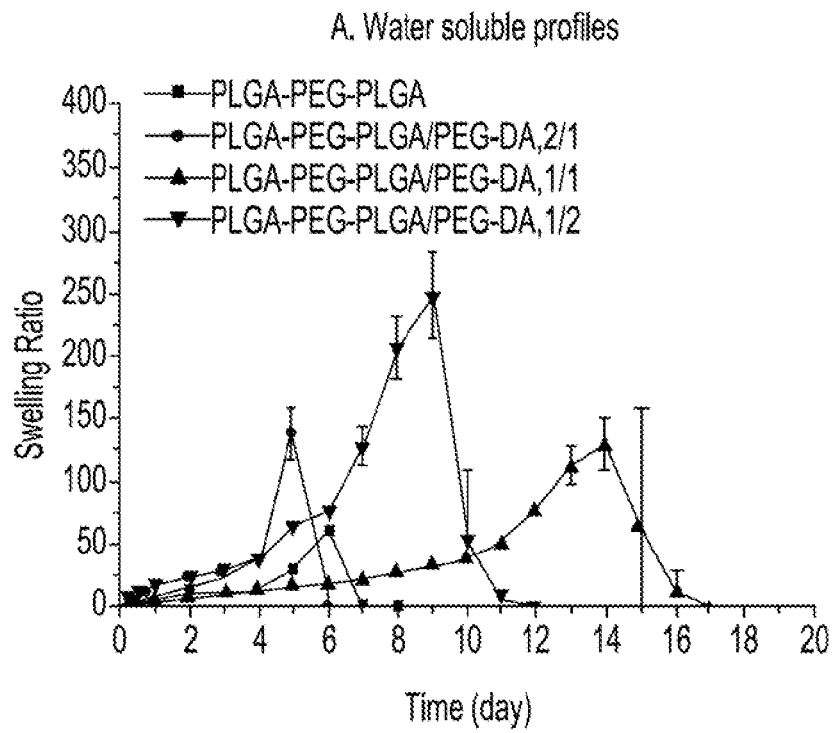
FIG. 5 shows two example expansion profiles, including water soluble profiles (A) and non-water-soluble profiles (B)
Figure 5:
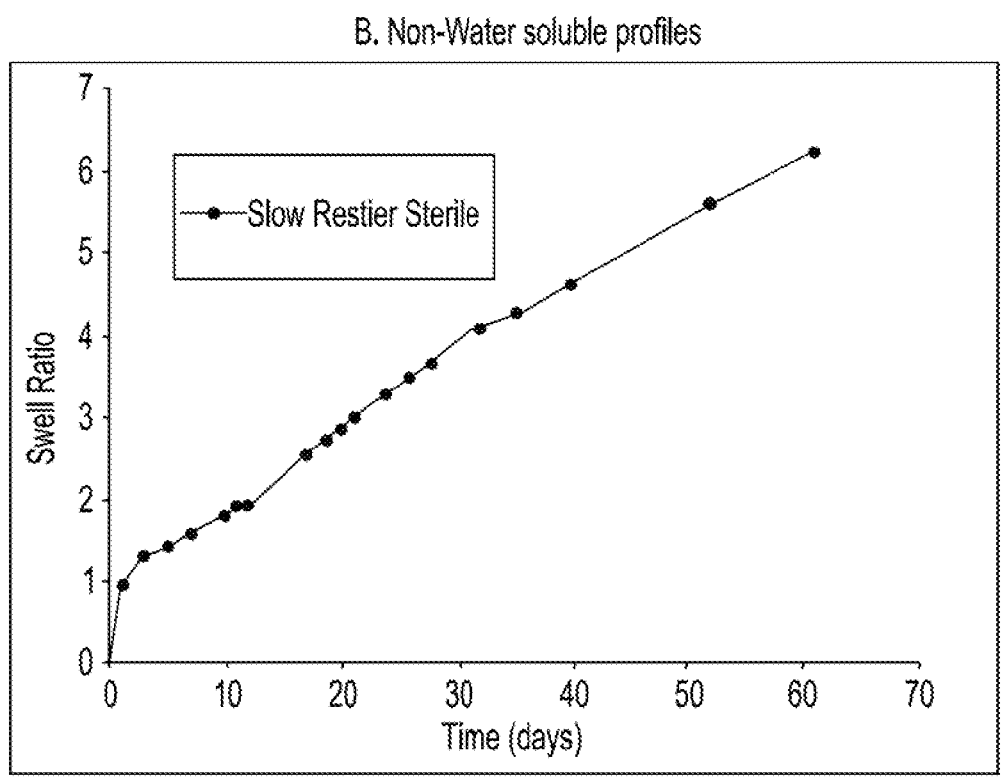

FIG. 5 shows two example expansion profiles to highlight a surprising result. Use of water-soluble triblocks creates hydrogels with a built-in-delay time prior to extremely rapid swelling and dissolution (see FIG. 5A for hydrogels synthesized from 333-1500-333 PLGA-PEG-PLGA-diacrylate and PEG-diacrylate (700 Da) at the indicated ratios). The scale on the vertical axis is in 100's of expansion ratio. This result is due to the fact that the hydrogel, completely comprised of water soluble components, is under extreme stress to expand during the entire period. Upon degradation, the chains are set free to expand rapidly. Generally, this property is well suited for situations wherein rapid, relatively large expansion is required. For the tissue expansion application, however, this is not necessarily desirable.

The use of non-water-soluble, triblock copolymers (e.g., PLGA-PEG-PLGA, in which the PLGA block size is substantially larger than the PEG block size) creates expanders which have lower initial swelling, as well as almost zero-order continuous swelling. This is due to the moderate increase in hydrophilicity of the entire expander as degradation removes hydrophobic PLGA components. This feature is valuable for the tissue expander application, as it allows for continuous expansion instead of the stepwise manner of the current injectable-saline expanders Continuous expansion generates less trauma to the tissue as pressure is maintained at an almost constant level.

In Vivo Testing: Rat Model

Hydrogels of the present invention were tested in an in-vivo setting. All animal testing was performed at the Laboratory Animal Resource Center (LARC) at Indiana University Medical School (IUMed) in accordance with the Institutional Animal Care and Use Committee (IACUC) of this university. All procedures were performed under anesthesia as appropriate for the animal and procedure.

Based on in-vitro results described above, Examples 20-24 were prepared and used in animal studies. For the following preparations, the concentration of ~20-25% w/v macromers in DMSO is fixed. As such, the formulations are described as % w/w of constituents.

Example 20

This hydrogel is prepared by reacting a (~20% w/v solids) DMSO solution containing 70.2% TB05-DA, 3.5% RG503 Ac, and 26.3% PEGDA (% w/w) components.

Example 21

This hydrogel is prepared by reacting a (~20% w/v solids) DMSO solution containing 45.1% TB05-DA, 6.4% RG503 Ac, 48.4% PEGDA, and 0.1% EGDiMAC (% w/w) components.

Example 22

This hydrogel is prepared by reacting a (~20% w/v solids) DMSO solution containing 60.5% TB05-DA, 9.1% RG503 Ac, 30.3% PEGDA, and 0.1% EGDiMAC (% w/w) components.

Example 23

This hydrogel is prepared by reacting a (~20% w/v solids) DMSO solution containing 63.2% TB05-DA, 4.8% RG503DA, 31.6% PEGDA, and 0.5% EGDiMAC (% w/w) components.

Example 24

This hydrogel has the same formulation as Example 17, but is coated with PVP (55 kDa) by briefly dipping the hydrogel in an aqueous solution of PVP and drying.

All hydrogels for animal studies were sterilized by ETO and handled aseptically prior to usage in the animal model. The pilot animal studies were performed on rats. Briefly, a section of tissue above the rats' skull was reflected, the implant was placed in beneath the tissue, and the wound was reclosed with stitches. The rats were then scanned with a 3D surface scanning FaroArm® laser device to precisely calculate the expansion area and volume three times per week. The rats were also observed for any signs of tissue reaction. An initial 18 rat pilot study was performed on 6 prototypes, and no tissue reactions such as necrosis or dehiscence were observed. One rat displayed light ulceration caused by rubbing of the head on the top of the cage, which was remedied by placing the food on the bottom of the cage. After 6 weeks of expansion, the rats were sacrificed and histology was performed on the harvested tissue sections. TABLE 5 shows initial expansion results from the pilot study. Several of the hydrogels expanded successfully, yet crumbled upon removal due to insufficient hydrophobic content and cross-linking.

TABLE 5

Expansion results from rat pilot study for Examples 19-24.

| Example | Tissue (%)[1] | End Condition |
| --- | --- | --- |
| 19 | 17/34/43 | Broken/pieces |
| 20 | 23/65/56 | Broken/pieces |
| 21 | 41/58/64 | Broken/pieces |
| 22 | 26/72/97 | Broken/pieces |
| 23 | 24/53/54 | Broken/pieces |
| 24 | 26/46/74 | Broken/pieces |

[1]surface area increase (%) of tissue at 2 days, 2 weeks, and 6 weeks, respectively.

This rat pilot study demonstrates that hydrogels with an appropriate combination of swelling rate and higher density of permanent cross-links have improved removability. This may be due to higher strength after full swelling. Based on this information, an additional five hydrogels were prepared and tested in 6 rats per each expander. Three rats were sacrificed after 4 weeks and the remaining after 6 weeks. As a control, 3 commercially purchased OSMED® expanders were implanted and tested in the same manner. The compositions of Examples 25-29 are as described in Table 6.

TABLE 6

Compositions of hydrogel Examples 25-29 and OSMED® control

| | Components (%, w/w) | | | | |
| --- | --- | --- | --- | --- | --- |
| Example | PLGA-PEG-PLGA (mw-mw-mw) Triblock Diacrylate | PLGA-acrylate (20k Da) | PEG Diacrylate (600 Da) (PEGDA) | Ethylene Glycol Dimethacrylate (EGDMA) | PEGDA + EGDMA |
| 25 | (7.5k-1k-7.5k) 58.0% | 8.7% | 29.0% | 4.3% | 33.3% |
| 26 | (7.5k-1k-7.5k) 70.0% | 0% | 26.2% | 3.8% | 30.0% |
| 27 | (5k-1k-5k) 78.6% | 11.1% | 4.9% | 5.4% | 10.3% |
| 28 | (5k-1k-5k) 40.0% | 17.2% | 42.8% | 0.1% | 42.9% |
| 29 | (5k-1k-5k) 39.3% | 5.6% | 42.1% | 12.9% | 55.0% |
| OSMED® (control) | Methylmethacrylate and N-vinylpyrrolidone copolymer with outer silicone rubber shell | | | | |

The resultant change in volume ratio (Volume(t)/Volume (i)) by expander was measured by analyzing the region of interest using the Faro arm scanner. TABLE 7 shows the resultant volume swelling at days ~3-4 (initial burst) and ~13-19 (delayed phase). Due to limitations on the number of animals handled on a single day, the timelines do not match exactly, but are very close to each other.

TABLE 7

Initial and delayed expansion volume of select Examples and OSMED ® control.

| Example | Initial expansion ratio (days) | Delayed expansion ratio (days) |
|---|---|---|
| 21 (N = 6) | 2.1 ± 1.4 (4.5 days) | 1.9 ± 1.1 (14.0 days) |
| 28 (N = 6) | 1.2 ± 0.6 (3.0 days) | 1.9 ± 1.5 (13.0 days) |
| 29 (N = 6) | 0.4 ± 0.5 (3.2 days) | 0.7 ± 0.8 (13.2 days) |
| OSMED ® control (N = 3) | 3.6 ± 1.1 (2.0 days) | 2.6 ± 0.4 (19.0 days) |

The tissues surrounding the expanders were histologically examined with statistical analysis. Chi-square tests were performed to determine if there were any significant differences among groups for blebs, chronic inflammation, or acute inflammation. Mantel-Haenszel tests for ordered categorical responses were performed to determine if there were any significant differences among groups for fibrous capsule, vascularity, or foam cell scores.

The results indicate that there were no statistically significant differences among groups for blebs (p=0.17), fibrous capsule (p=0.30), chronic inflammation (p=0.30), foam cells (p=0.06) or acute inflammation (p=1.00). Example 29 had significantly higher vascularity scores than most other groups. The full histological scores are shown in TABLE 8. The best performer in terms of reduced initial expansion with slow expansion was Example 29. This expander also presented good clinical behavior in terms of ease of insertion and removal and had notably less crumbling than other expander prototypes. As noted in the last column of TABLE 6, Example 29 has the highest total concentration of non-degradable cross-linkers (55.0% of PEGDA+EGDMA). Thus, Example 29 was identified as a logical candidate for a dog study.

TABLE 8

Histological scores for select hydrogel expander Examples.

| Category | Example-weeks at necropsy | Scores (%) 0 | 1 | 2 | 3 | 4 | p-Value |
|---|---|---|---|---|---|---|---|
| Blebs | Example 21-4 | 0 (0%) | 3 (100%) | | | | 0.17 |
| | Example 21-6 | 1 (33%) | 2 (67%) | | | | |
| | Example 22-4 | 1 (33%) | 2 (67%) | | | | |
| | Example 22-6 | 1 (33%) | 2 (67%) | | | | |
| | Example 23-4 | 0 (0%) | 3 (100%) | | | | |
| | Example 22-6 | 2 (67%) | 1 (33%) | | | | |
| | Example 25-4 | 1 (33%) | 2 (67%) | | | | |
| | Example 25-6 | 0 (0%) | 3 (100%) | | | | |
| | Example 26-4 | 3 (33%) | 2 (67%) | | | | |
| | Example 26-6 | 0 (0%) | 3 (100%) | | | | |
| | Example 27-4 | 3 (50%) | 1 (50%) | | | | |
| | Example 27-6 | 3 (33%) | 2 (67%) | | | | |
| | Example 28-6 | 0 (0%) | 3 (100%) | | | | |
| | Example 28-4 | 2 (67%) | 1 (33%) | | | | |
| | Example 29-4 | 1 (33%) | 2 (67%) | | | | |
| | Example 29-6 | 0 (0%) | 3 (100%) | | | | |
| | Example 18-4 | 0 (0%) | 3 (100%) | | | | |
| | Example 18-6 | 0 (0%) | 3 (100%) | | | | |
| | OSMED ®-0611 | 3 (100%) | 0 (0%) | | | | |
| Fibrous Capsule | Example 21-4 | | 0 (0%) | 0 (0%) | 3 (100%) | 0 (0%) | 0.30 |
| | Example 21-6 | | 0 (0%) | 2 (67%) | 1 (33%) | 0 (0%) | |
| | Example 22-4 | | 0 (0%) | 2 (67%) | 1 (33%) | 0 (0%) | |
| | Example 22-6 | | 0 (0%) | 2 (67%) | 1 (33%) | 0 (0%) | |
| | Example 23-4 | | 0 (0%) | 0 (0%) | 2 (67%) | 1 (33%) | |
| | Example 23-6 | | 1 (33%) | 1 (33%) | 1 (33%) | 0 (0%) | |
| | Example 25-4 | | 0 (0%) | 1 (33%) | 2 (67%) | 0 (0%) | |
| | Example 25-6 | | 0 (0%) | 2 (67%) | 1 (33%) | 0 (0%) | |
| | Example 26-4 | | 0 (0%) | 1 (33%) | 2 (67%) | 0 (0%) | |
| | Example 26-6 | | 0 (0%) | 2 (67%) | 1 (33%) | 0 (0%) | |
| | Example 27-4 | | 1 (33%) | 2 (67%) | 0 (0%) | 0 (0%) | |
| | Example 27-6 | | 0 (0%) | 3 (100%) | 0 (0%) | 0 (0%) | |
| | Example 28-6 | | 0 (0%) | 2 (67%) | 0 (0%) | 1 (33%) | |
| | Example 28-4 | | 0 (0%) | 2 (67%) | 1 (33%) | 0 (0%) | |
| | Example 29-4 | | 0 (0%) | 1 (33%) | 1 (33%) | 1 (33%) | |
| | Example 29-6 | | 0 (0%) | 2 (67%) | 1 (33%) | 0 (0%) | |
| | Example 18-4 | | 0 (0%) | 0 (0%) | 1 (33%) | 2 (67%) | |
| | Example 18-6 | | 0 (0%) | 2 (67%) | 1 (33%) | 0 (0%) | |
| | OSMED ®-0611 | | 0 (0%) | 1 (33%) | 2 (67%) | 0 (0%) | |
| Chronic Inflammation | Example 21-4 | 2 (67%) | 1 (33%) | | | | 0.30 |
| | Example 21-6 | 3 (100%) | 0 (0%) | | | | |
| | Example 22-4 | 2 (67%) | 1 (33%) | | | | |
| | Example 22-6 | 3 (100%) | 0 (0%) | | | | |
| | Example 23-4 | 2 (67%) | 1 (33%) | | | | |
| | Example 23-6 | 2 (67%) | 1 (33%) | | | | |
| | Example 25-4 | 2 (67%) | 1 (33%) | | | | |
| | Example 25-6 | 3 (100%) | 0 (0%) | | | | |
| | Example 26-4 | 3 (100%) | 0 (0%) | | | | |
| | Example 26-6 | 3 (100%) | 0 (0%) | | | | |
| | Example 27-4 | 1 (33%) | 2 (67%) | | | | |
| | Example 27-6 | 2 (67%) | 1 (33%) | | | | |
| | Example 28-6 | 2 (67%) | 1 (33%) | | | | |

TABLE 8-continued

Histological scores for select hydrogel expander Examples.

| Category | Example-weeks at necropsy | Scores (%) 0 | 1 | 2 | 3 | 4 | p-Value |
|---|---|---|---|---|---|---|---|
| | Example 28-4 | 2 (67%) | 1 (33%) | | | | |
| | Example 29-4 | 0 (0%) | 3 (100%) | | | | |
| | Example 29-6 | 3 (100%) | 0 (0%) | | | | |
| | Example 18-4 | 2 (67%) | 1 (33%) | | | | |
| | Example 18-6 | 3 (100%) | 0 (0%) | | | | |
| | OSMED ®-0611 | 2 (67%) | 1 (33%) | | | | |
| Vascularity | Example 21-4 | 0 (0%) | 0 (0%) | 3 (100%) | 0 (0%) | | 0.0327 |
| | Example 21-6 | 0 (0%) | 2 (67%) | 1 (33%) | 0 (0%) | | |
| | Example 22-4 | 0 (0%) | 2 (67%) | 1 (33%) | 0 (0%) | | |
| | Example 22-6 | 0 (0%) | 2 (67%) | 1 (33%) | 0 (0%) | | |
| | Example 23-4 | 0 (0%) | 2 (67%) | 1 (33%) | 0 (0%) | | |
| | Example 23-6 | 0 (0%) | 2 (67%) | 1 (33%) | 0 (0%) | | |
| | Example 25-4 | 1 (33%) | 2 (67%) | 0 (0%) | 0 (0%) | | |
| | Example 25-6 | 0 (0%) | 1 (33%) | 2 (67%) | 0 (0%) | | |
| | Example 26-4 | 0 (0%) | 2 (67%) | 1 (33%) | 0 (0%) | | |
| | Example 26-6 | 0 (0%) | 2 (67%) | 1 (33%) | 0 (0%) | | |
| | Example 27-4 | 0 (0%) | 2 (67%) | 1 (33%) | 0 (0%) | | |
| | Example 27-6 | 0 (0%) | 3 (100%) | 0 (0%) | 0 (0%) | | |
| | Example 28-6 | 0 (0%) | 1 (33%) | 2 (67%) | 0 (0%) | | |
| | Example 28-4 | 0 (0%) | 1 (33%) | 2 (67%) | 0 (0%) | | |
| | Example 29-4 | 0 (0%) | 0 (0%) | 0 (0%) | 3 (100%) | | |
| | Example 29-6 | 0 (0%) | 1 (33%) | 2 (67%) | 0 (0%) | | |
| | Example 18-4 | 0 (0%) | 1 (33%) | 2 (67%) | 0 (0%) | | |
| | Example 18-6 | 0 (0%) | 1 (33%) | 2 (67%) | 0 (0%) | | |
| | OSMED ®-0611 | 0 (0%) | 1 (33%) | 2 (67%) | 0 (0%) | | |
| Foam Cells | Example 21-4 | 1 (33%) | 1 (33%) | 0 (0%) | 1 (33%) | 0 (0%) | 0.06 |
| | Example 21-6 | 1 (33%) | 1 (33%) | 1 (33%) | 0 (0%) | 0 (0%) | |
| | Example 22-4 | 0 (0%) | 0 (0%) | 2 (67%) | 1 (33%) | 0 (0%) | |
| | Example 22-6 | 0 (0%) | 0 (0%) | 2 (67%) | 0 (0%) | 1 (33%) | |
| | Example 23-4 | 0 (0%) | 1 (33%) | 1 (33%) | 1 (33%) | 0 (0%) | |
| | Example 23-6 | 1 (33%) | 2 (67%) | 0 (0%) | 0 (0%) | 0 (0%) | |
| | Example 25-4 | 0 (0%) | 3 (100%) | 0 (0%) | 0 (0%) | 0 (0%) | |
| | Example 25-6 | 0 (0%) | 1 (33%) | 1 (33%) | 1 (33%) | 0 (0%) | |
| | Example 26-4 | 1 (33%) | 2 (67%) | 0 (0%) | 0 (0%) | 0 (0%) | |
| | Example 26-6 | 0 (0%) | 3 (100%) | 0 (0%) | 0 (0%) | 0 (0%) | |
| | Example 27-4 | 1 (33%) | 2 (67%) | 0 (0%) | 0 (0%) | 0 (0%) | |
| | Example 27-6 | 1 (33%) | 2 (67%) | 0 (0%) | 0 (0%) | 0 (0%) | |
| | Example 28-6 | 0 (0%) | 2 (67%) | 1 (33%) | 0 (0%) | 0 (0%) | |
| | Example 28-4 | 3 (100%) | 0 (0%) | 0 (0%) | 0 (0%) | 0 (0%) | |
| | Example 29-4 | 2 (67%) | 1 (33%) | 0 (0%) | 0 (0%) | 0 (0%) | |
| | Example 29-6 | 0 (0%) | 3 (100%) | 0 (0%) | 0 (0%) | 0 (0%) | |
| | Example 18-4 | 1 (33%) | 1 (33%) | 1 (33%) | 0 (0%) | 0 (0%) | |
| | Example 18-6 | 0 (0%) | 2 (67%) | 0 (0%) | 1 (33%) | 0 (0%) | |
| | OSMED ®-0611 | 0 (0%) | 1 (33%) | 1 (33%) | 1 (33%) | 0 (0%) | |
| Acute Inflammation | Example 21-4 | 3 (100%) | | | | | 1.00 |
| | Example 21-6 | 3 (100%) | | | | | |
| | Example 22-4 | 3 (100%) | | | | | |
| | Example 22-6 | 3 (100%) | | | | | |
| | Example 23-4 | 3 (100%) | | | | | |
| | Example 23-6 | 3 (100%) | | | | | |
| | Example 25-4 | 3 (100%) | | | | | |
| | Example 25-6 | 3 (100%) | | | | | |
| | Example 26-4 | 3 (100%) | | | | | |
| | Example 26-6 | 3 (100%) | | | | | |
| | Example 27-4 | 3 (100%) | | | | | |
| | Example 27-6 | 3 (100%) | | | | | |
| | Example 28-6 | 3 (100%) | | | | | |
| | Example 28-4 | 3 (100%) | | | | | |
| | Example 29-4 | 3 (100%) | | | | | |
| | Example 29-6 | 3 (100%) | | | | | |
| | Example 18-4 | 3 (100%) | | | | | |
| | Example 18-6 | 3 (100%) | | | | | |
| | OSMED ®-0611 | 3 (100%) | | | | | |

In-Vivo Testing: Dog Model

For this initial study, the molar teeth of both the maxillary and mandibular section from both sides of 2 beagle dogs were extracted, and the ridge ground down to model the natural process of bone resorption in humans. After 3 months of healing, the dogs had 6 Example 29 expanders and 2 OSMED®$^{gmbh}$ control expanders surgically placed in either the left or right mandible or maxillary section of the jaw in a random block pattern. Example 29 expanders were reshaped by the surgeon at time of emplacement. The OSMED® type 400-1070 expanders were inserted with a screw mounting to the bone as per manufacturer's directions.

The expanders were allowed to expand in the mucosa tissue for four weeks, or until secondary endpoint of tissue expander self-removal ("popping out"). At predetermined time points, dental impression and casts were made over the expanded tissue, and removed for future use in assaying expansion. After the 4-week time frame, a biopsy of the expanded mucosa was taken and the mucosa re-sutured to allow healing without sacrificing the dogs.

The OSMED® control expanders both self-removed from the mucosa within 12 days of emplacement. This occurred via expulsion directly through the mucosa. One of the Example 29 hydrogels also underwent expulsion via a very similar pattern after 19 days of emplacement. In each case, expulsion occurred directly through the tissue rather than at the sutured point, indicating that time to suture healing was not the mechanism/problem that leads to these expanders being lost through the mucosa. Of the 5 remaining expander prototypes at the end of the study, only 2 were found and recovered in a maxilla of one of the dogs. The remaining 3 broke down and could not be recovered. Of the expanders that could be removed, all were observed to be fractured but remained in large enough pieces to allow traditional surgical removal using forceps and conventional surgical tools.

The initial results of the dog study are surprising. The expansion of mucosal tissue apparently requires a substantially-altered hydrogel relative to the Example 29 design. This requires further understanding on the relationship between hydrogel properties and in vivo results. The expulsion of the expander indicates higher expansion pressure than the tissue can bear, and the fractured expander indicates the weak/brittle nature of the expanded hydrogel.

Figure 6:
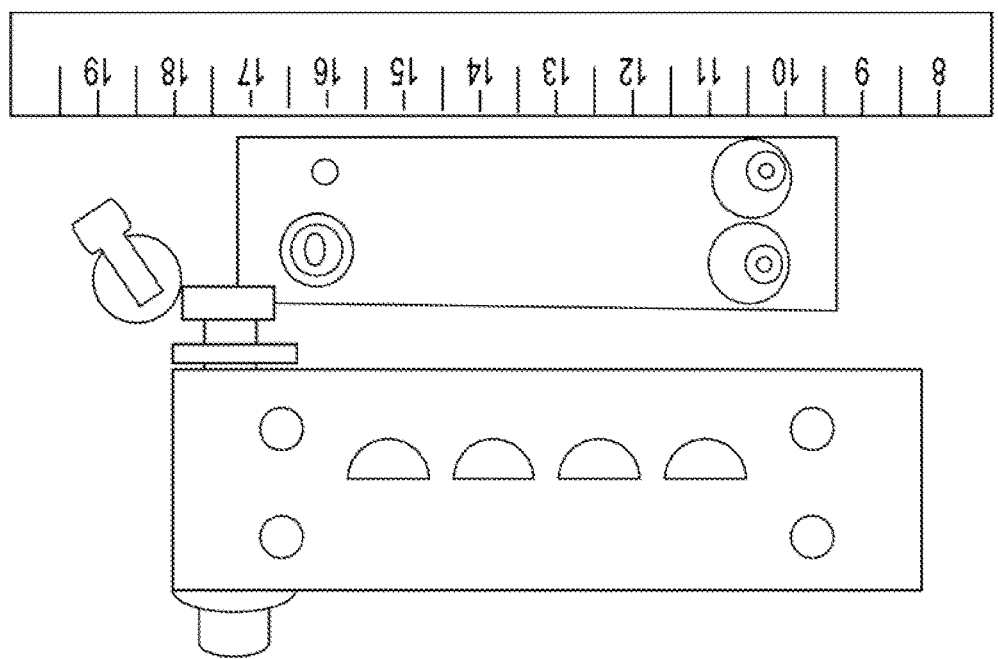
FIG. 6 show a half-cylinder mold, useful in the production of the hydrogels of the present invention.

To aid in visualizing and tracking the expanders, a fluorescent fluorescein diacrylate dye was incorporated into the hydrogel structure. Thus, a new set of expander prototypes was synthesized. Of more than 80 new prototypes generated, two fluorescein-labeled versions (Example 30 and Example 31) were selected based on the in vitro properties for the dog study. Additionally, Example 32 was selected as a prototype that has similar expansion properties but has substantially improved end strength. (see Table rounded point on the terminal end to aid in implantation. This was accomplished by carrying out the reactions in a half-cylinder mold, as shown in FIG. 6.

Six Example 30 expanders were placed in right maxillary and mandibular positions, while six of Example 31 were placed in left maxillary and mandibular positions. Since the expanders were already semi-cylindrical, reshaping the expander at time of emplacement was limited to adjusting the length of the hydrogel for insertion. The expanders were allowed to expand in the mucosa tissue for approximately 6 weeks. The results showed that four of the Example 30 expanders were expelled by necropsy day (44 days after implantation), while all of Example 31 expanders remained intact at the implantation sites. The data clearly demonstrates that Example 31 expanders performed better than Example 30 expanders. Furthermore, Example 31 expanders were observed to generate clinically useful flaps of tissue after 6 weeks of expansion, and remained intact even after recovery from the dog.

Figure 7:
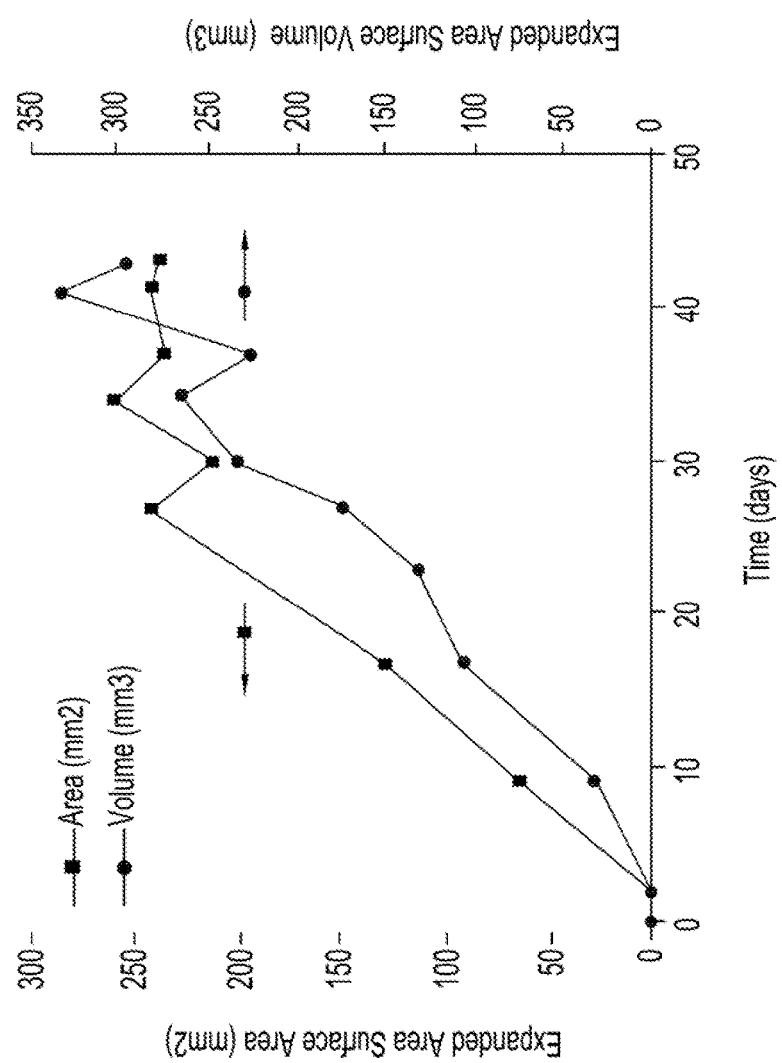
FIG. 7 is a graphic illustration of the expansion kinetics for Example 31.

In vivo expansion of the inserted expanders was measured using a 3D scanning Faro-arm device. FIG. 7 shows expansion kinetics for Example 31. The increase in the expanded area volume matches with formation of new tissue. The kinetic data in FIG. 7 indicates that the expansion reaches plateau in about 4-6 weeks.

The histology and clinical notations ascertained from the animal studies indicate that the novel hydrogel expander materials of the invention are highly biocompatible and non-toxic and further investigated by biocompatibility testing of Example 32. This hydrogel was selected as it is chemically similar to Example 31, but does not contain fluorescein diacrylate that is intended only for tracking purposes, and not for inclusion in a clinical material. Cytotoxicity and biocompatibility testing of Example 32 were performed by Toxikon Corporation (Bedford, Mass.). The tests/regulatory # performed include: L929-MEM elution/ISO10993-5, Intracutaneous injection/ISO10993-10, Systemic injection/ISO10993-11, Rabbit pyrogen test/ISO10993-11, Muscle implant 7-Day/USP 34, NF-29, Reverse mutation assay/ISO10993-3, and Particulate matter

TABLE 9

Hydrogel expander Examples 30-32, with Example 29 shown for comparison.

| | Components (%, w/w) | | | | | In vitro Properties | | |
|---|---|---|---|---|---|---|---|---|
| Ex. | PLGA-PEG-PLGA (5k-1k-5k) Triblock Diacrylate | Polyester Acrylates * | PEG Diacrylate (600 Da) | Ethylene glycol dimethacrylate | Fluoroscein Diacrylate | Initial Swelling (Day 1-3) | Overall Swelling (Day 42) | End Strength (N/mm) |
| 29 | 39.3% | (PLG1) 5.6% | 42.1% | 12.9% | 0% | 170% | 246% | 0.49 |
| 30 | 45.8% | (PLG2) 9.8% | 32.7% | 9.8% | 1.6% | 168% | 340% | 1.61 |
| 31 | 41.0% | (PL2) 4.1% | 41.0% | 12.6% | 1.0% | 173% | 269% | 0.57 |
| 32 | 41.4% | (PL2) 4.1% | 41.5% | 12.8% | 0% | 187% | 250% | 2.12 |

* (PLG1: RG503DA; PLG2: PLGA-diacrylate (8.7 kDa); PL2: PLA-diacrylate (8.7 kDa))

In addition to modifying in-vitro properties of the hydrogel, the initial shape of the expanders was adjusted to be substantially a "half-moon." This is clinically beneficial based on its capacity to expand without exposing tissue to an expander's corners or sharp edges. Additionally, the half-moon, cross-section of a cylinder-shaped expander has a by light obscuration/USP 34, NF-29. The results of the tests indicate that there is no cytotoxicity, no intracutaneous toxicity, no system toxicity, no sign of pyrogenic response, no significant biological response, same colonies as compared to negative controls, and average of 18.9 particles/ml (>10 μm) and 3.7 particles/ml (>25 μm). Overall, these tests indicate an extremely well-tolerated material with minimal biological toxicity. Thus, this material is considered to be highly biocompatible.

Despite the success of some Examples in the in-vivo dog model, in some situations failure still occurred Thus, Example 33 was prepared for in-vivo dog testing.

Example 33

This hydrogel was synthesized as previously described, containing (% w/w) 37.6% PLGA-PEG-PLGA, 37.6% PEGDA (600), 11.6% Ethylene glycol dimethacrylate, and 13.2% PLA-diacrylate (8.7 kDa) with total concentration w/v solids of 27% in DMSO. The initial $1^{st}$ day swelling for this example was 171%, with final swelling of 242%.

Examples 32 and 33 were tested in the dog jawbone model as previously described. Of 4 expanders tested, Example 32 had 2 which were not found at necropsy, and 2 which were removed as crumbled pieces. Example 33 had 2 removed as one piece and 2 removed as crumbled pieces, indicating that this example is improved over Example 32.

Examples 34-39 were prepared to validate a material meeting the required in-vitro properties of Examples 30 and 31, without the addition of fluorescein diacrylate, as this is undesirable from a regulatory perspective. For this work, the % w/v solvents in DMSO was varied, as indicated in TABLE 10.

TABLE 10

Compositions of hydrogel Examples 34-39.

| | | | Component (% w/w) | | | |
|---|---|---|---|---|---|---|
| Example | Tribiock diacrylate | Polyester Diacrylate | PEG Diacrylate (600 Da) | Ethylene Glycol dimethacrylate | Lauryl methacrylate | Solids (% w/v) |
| 34 | 41.4% TB11DA | 4.7% PLG-DMA | 41.4% | 12.4% | 0.0% | 24% |
| 35 | 38.5% TB11DA | 5.1% PL-DA | 38.5% | 11.5% | 6.4% | 25% |
| 36 | 51.9% TB10DA | 5.2% PL-DA | 26.0% | 10.40% | 6.5% | 22% |
| 37 | 48.2% TB10DA | 14.5% PLG-DMA | 24.1% | 7.20% | 6.0% | 24% |
| 38 | 56.3% TB10DA | 5.6% PL-DA | 28.2% | 9.90% | 0.0% | 21% |
| 39 | 51.9% TB10DA | 15.6% PLG-DMA | 26.0% | 6.50% | 0.0% | 22% |

Table 10 acronym key: PLG-DMA: PLGA-DMA (1:1, 9000 Da); PL-DA: P(DL)La-DA (70,000)

Examples 34-39 were assayed in-vitro as described above, with the resulting characteristics shown in TABLE 11.

TABLE 11

In-vitro characterization of Examples 34-39.

| Example | Initial swelling (Day 1) | Full swelling (Day 42-60) | End Strength (N/mm) |
|---|---|---|---|
| 34 | 272% | 310% | 2.50 |
| 35 | 226% | 277% | 2.68 |
| 36 | 128% | 230% | 2.48 |
| 37 | 135% | 256% | 1.41 |
| 38 | 137% | 223% | 1.76 |
| 39 | 145% | 346% | 0.45 |

Example 34, which is similar to Example 31 in composition except with use of PLA-PEG-PLA triblock instead of PLGA-PEG-PLGA triblock, had unfavorable initial swelling. Similarly, Example 35, which is similar with the addition of hydrophobicizing-agent laural methacrylate, also has unfavorable initial swelling. These results demonstrate that desirable compositions of the prototype expanders is unobvious, as the addition of the more highly hydrophobic PLA chains and lauryl methacrylate should logically lead to lower initial swelling. The compositions comprising PLA-PEG-PLA were observed to be opaque and cloudy, indicating phase transition within the matrix. This result indicates that for medical expander use, a PLGA-PEG-PLGA polymer is desirable. Examples 36-39 show that expanders with superior in-vitro properties can be obtained utilizing PLGA-PEG-PLGA (TB10) along with lauryl methacrylate or without it.

Example 40 further demonstrates the non-obvious nature of the hydrogel properties. It is similar to Example 38, with the exception of slightly more ethylene glycol dimethacrylate and PEG (256 Da) diacrylate, rather than PEG (600 Da) diacrylate.

Example 40

This hydrogel is synthesized as previously described using 55.6% TB11-DA, 5.6% P(DL)La-DA (70,000), 27.8% PEG-DA (256 Da), and 11.1% ethylene glycol dimethacrylate (21% w/v solids).

Notably, Example 40 is observed to be hard and crystalline, similar to chalk in texture. Despite the slight changes in ingredients, this prototype could not be cut or modified due to its brittle nature. Similarly, Example 41 demonstrates issues associated with too low of cross-linking. This hydrogel is synthesized by reacting 20% w/v TB11DA directly. The gelling observed is inconsistent, and an unsuitable quantity of solid is obtained, with a majority of material remaining substantially liquid.

The nature of the novel hydrogels described herein is that their mechanical and swelling properties are determined by a complex interplay of various components. Unlike typical hydrogels, which are primarily mixtures of monomers with a relatively low quantity of cross-linkers, the hydrogels of the invention are substantially comprised of cross-linker components. The cross-linking density of these new hydrogels is not controlled so much by the molar ratio of multi-vinyl components to monomeric units, but rather by the molecular weight of the multivinyl units. For this reason, traditional methods of calculating cross-linking density (i.e., moles cross-linker/moles monomer) are unsuitable for describing the cross-linking of these hydrogels. Instead, the cross-linking density can be considered based on relative number of vinyl units as compared to chain length of the macromer. On a per mole basis, TB05-DA contains 2 vinyl active units per ~11 kDa of polymer chain, equivalent to 0.18 VI/kDa (number vinyl units/kilodalton macromer). Respectively, other cross-linkers could be ranked with their relative VI/kDa, as shown in TABLE 12

TABLE 12

Relative VI/kDa for Select Example macromers

| Macromer | VI/kDa | Macromer | VI/kDa |
|---|---|---|---|
| TB05-DA | 0.18 | Poly(ethylene glycol) diacrylate (600 Da) | 3.33 |
| PLGA-DMA (1:1, 9000 Da) | 0.22 | Ethylene glycol dimethacrylate | 10.09 |
| PL-DA: P(DL)La-DA (70,000) | 0.03 | PLGA-diacrylate (8.7 kDa) | 0.23 |
| TB10-DA | 0.25 | TB09-DA | 0.13 |
| Fluorescein diacrylate | 4.54 | TB01-DA | 0.92 |

It should be noted that monomers do not contribute to cross-linking density. Multiplying the mass % content of the Example hydrogel's components by its respective VI/kDa can give the relative molar contribution of each macromer to the cross-linking density. Adding these together gives the cross-linking density of the example in #cross-links/mg or "Q," as cross-linking density is commonly referred to.

The relative cross-linking density is shown for a series of Examples in TABLE 13. Cross-linking density is important to controlling the swelling as well as the mechanical properties. In situations where the cross-linking density is too high, the material is brittle and cannot be cut or properly emplaced. If the cross-linking density is too low, the resultant material is too soft and swells rapidly to a large size.

TABLE 13

Initial calculated cross-linking density for select Examples

| Example | Calculated crosslink density (links/mg) Q |
|---|---|
| 29 | 2.79 |
| 30 | 2.26 |
| 31 | 2.77 |
| 32 | 2.76 |
| 34 | 2.71 |
| 35 | 2.51 |
| 36 | 2.05 |
| 37 | 1.68 |
| 38 | 2.08 |
| 39 | 1.69 |
| 40 (too high crosslinking) | 3.39 |
| 41 (too low crosslinking) | 0.18 |

In addition to cross-linking density, the expansion properties of the hydrogels are controlled by the relative hydrophobic/hydrophilic contributions of the various components. Although this is a complex system and hydrophobic/hydrophilic are relative terms, generally it can be understood that the polyester chains, which are not normally water soluble, are considerably more hydrophobic than the poly(ethylene glycol) chains and the polyacrylate backbones.

Additionally, additives such as lauryl methacrylate and ethylene glycol dimethacrylate increase the overall hydrophobicity, even though ethylene glycol dimethacrylate has a greater impact on cross-linking. For the triblock copolymers, the hydrophobic/hydrophilic contribution can be calculated as the ratio of their total PLGA MW to their total MW. For instance, TB05-DA can be calculated to have a hydrophobic contribution of 10,000 Da (PLGA)/11,000 Da (total)=0.91.

Purely hydrophobic components (PLGA diacrylate and ethylene glycol dimethacrylate) can be considered to contribute 1× to hydrophobicity, and hydrophilic items (PEG diacrylate) can be considered to contribute 1× to hydrophilicity. Multiplying the hydrophic contributions of each component (PEGDA=0) by the % w/w content in the expander allows for the overall hydrophobicity of the expander to be calculated in terms of % hydrophobic. TABLE 14 shows initial hydrophobicity of select Examples. Example 1 is included to show an expander with substantially unsuitable initial hydrophobicity.

TABLE 14

Select expanders calculated initial hydrophobicity.

| Example | Hydrophobic content (%) | Example # | Hydrophobic content (%) |
|---|---|---|---|
| Example 1 (too low hydrophobicity) | 31% | 39 | 68% |
| 36 | 68% | 29 | 54% |
| 37 | 70% | 32 | 55% |
| 38 | 65% | 22 | 59% |

It should be noted that die cross-linking density and the hydrophobic/hydrophilic contributions all play a role in defining the swelling of the hydrogel. This quantity is dynamic, however, as upon hydrolysis the decrease in PLGA/PLA content relative to hydrolytically-stable hydrophilic components, such as PEG and polyacrylic acid, decreases the overall hydrophobicity of the material and severs cross-links, thereby increasing the swelling.

The mechanical properties of materials are also important for tissue expanders. They must allow the expander to be trimmed to size and placed under the tissue by tunneling or similar surgical techniques. For this reason the material must not be too hard or too soft. A series of prototypes displaying good mechanical properties for implantation are shown in TABLE 15.

TABLE 15

Mechanical properties of select Examples

| Example | Modulus of Elasticity (kPa, 2% strain) | Stress Relaxation (%) |
|---|---|---|
| 25 | 2.1 | 23.1 |
| 29 | 9.5 | 51.6 |
| 30 | 3.0 | 36.4 |
| 31 | 5.5 | 51.2 |
| 32 | 9 | 55 |
| 32 | 6.6 | 48.9 |
| 33 | 8.5 | 51.2 |
| 36 | 10.6 | 27.0 |
| 37 | 3.5 | 28.2 |
| 38 | 2.6 | 27.8 |
| 39 | 3.7 | 28.9 |

The invention claimed is:
1. A hydrophobic hydrogel, chemically-cross-linked via ester-acrylate bonds, comprising: triblock $(PLGA)_x$-

$(PEG)_y$-$(PLGA)_z$ copolymers having molecular weights of 1,000 to 50,000 Da, wherein: the percent ratio of ((molecular weight of total PLGA)/(molecular weight of total copolymer)×100%) for the copolymers is >60%; and each of x, y, and z is independently an integer from 1 to 500; wherein the cross-linking density of the hydrogel (trilinked chains/mg) is 0.1 to 5.0; and, wherein the overall hydrophobicity (directly water insoluble content/water soluble content) is 35% to 90%.

2. The hydrogel of claim 1, wherein the triblock $(PLGA)_x$-$(PEG)_y$-$(PLGA)_z$ copolymers have molecular weights of 2,000 to 40,000 Da.

3. The hydrogel of claim 1, wherein the percent ratio of ((molecular weight of total PLGA)/(molecular weight of total copolymer)×100%) for the copolymers is 95-75%.

4. The hydrogel of claim 1, wherein the triblock $(PLGA)_x$-$(PEG)_y$-$(PLGA)_z$ copolymers comprise 1% to 80% (w/w) of the hydrogel.

5. The hydrogel of claim 1, wherein the lactide:glycolide ratio in the $(PLGA)_x$ copolymer ranges from about 50:50 to about 99:1.

6. The hydrogel of claim 1, wherein $(PLGA)_x$ is about 1000 to about 7000 Da, $(PEG)_y$ is about 200 to about 2000 Da, and $(PLGA)_z$ is about 1000 to about 7000 Da.

7. The hydrogel of claim 1, wherein x=z.

8. The hydrogel of claim 1, further comprising (PLGA)- or (PLA)-diacrylates having molecular weights of 1,000 to 200,000 Da.

9. The hydrogel of claim 8, wherein the concentration of the (PLGA)- or (PLA)-diacrylates is 1% to 30% (w/w) of the hydrogel.

10. The hydrogel of claim 8, wherein the lactide:glycolide ratio in the (PLGA)-diacrylate copolymer ranges from about 50:50 to about 99:1.

11. The hydrogel of claim 1, further comprising poly (ethylene glycol) diacrylates having molecular weights of 100 to 10,000 Da.

12. The hydrogel of claim 11, wherein the concentration of the poly(ethylene glycol) diacrylates is 5% to 70% (w/w) of the hydrogel.

13. The hydrogel of claim 1, further comprising ethylene glycol dimethacrylate as a crosslinker.

14. The hydrogel of claim 13, wherein the ethylene glycol dimethacrylate has a concentration of 1% to 30% (w/w) of the hydrogel.

15. The hydrogel of claim 1, wherein the hydrogel is impregnated with one or more drugs selected from: a growth factor, an antibiotic, a pain-relieving drug, a blood-coagulation modifying agent, and an immune-response modifying agent.

16. A hydrophobic hydrogel, chemically-cross-linked via ester-acrylate bonds, comprising: triblock $(PLGA)_x$-$(PEG)_y$-$(PLGA)_z$ copolymers having molecular weights of 1,000 to 50,000 Da, wherein: the percent ratio of ((molecular weight of total PLGA)/(molecular weight of total copolymer)×100%) for the copolymers is >60%; and each of x, y, and z is independently an integer from 1 to 500; wherein the cross-linking density of the hydrogel (trilinked chains/mg) is 0.1 to 5.0; and, wherein the overall hydrophobicity (directly water insoluble content/water soluble content) is 35% to 90%;

wherein the hydrogel further comprises (PLGA)- or (PLA)-diacrylates having molecular weights of 1,000 to 200,000 Da; and, wherein the concentration of the (PLGA)- or (PLA)-diacrylates is 1% to 30% (w/w) of the hydrogel.

17. A hydrophobic hydrogel, chemically-cross-linked via ester-acrylate bonds, comprising: triblock $(PLGA)_x$-$(PEG)_y$-$(PLGA)_z$ copolymers having molecular weights of 1,000 to 50,000 Da, wherein: the percent ratio of ((molecular weight of total PLGA)/(molecular weight of total copolymer)×100%) for the copolymers is >60%; and each of x, y, and z is independently an integer from 1 to 500; wherein the cross-linking density of the hydrogel (trilinked chains/mg) is 0.1 to 5.0; and, wherein the overall hydrophobicity (directly water insoluble content/water soluble content) is 35% to 90%;

wherein the hydrogel is further impregnated with one or more drugs selected from: a growth factor, an antibiotic, a pain-relieving drug, a blood-coagulation modifying agent, and an immune-response modifying agent.

* * * * *